United States Patent
Petrosenko et al.

(10) Patent No.: US 7,557,718 B2
(45) Date of Patent: Jul. 7, 2009

(54) LACK OF PATIENT MOVEMENT MONITOR AND METHOD

(75) Inventors: Robert Petrosenko, Daniel Island, SC (US); David Lokhorst, Victoria (CA); Mayur Yermaneni, Cincinnati, OH (US); Michael Z. Sleva, Wyoming, OH (US); William L. Jacques, II, Mt. Pleasant, SC (US); Karen Janoff, Mt. Pleasant, SC (US); John A. Bobey, Daniel Island, SC (US); Jonathan H. Mueller, Mt. Pleasant, SC (US); Richard B. Stacy, Daniel Island, SC (US); Andrew F. Skinner, Batesville, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 626 days.

(21) Appl. No.: 11/119,635

(22) Filed: May 2, 2005

(65) Prior Publication Data

US 2005/0273940 A1   Dec. 15, 2005

Related U.S. Application Data

(60) Provisional application No. 60/567,215, filed on Apr. 30, 2004, provisional application No. 60/665,241, filed on Mar. 25, 2005, provisional application No. 60/665,141, filed on Mar. 25, 2005, provisional application No. 60/636,252, filed on Dec. 15, 2004, provisional application No. 60/608,013, filed on Sep. 8, 2004.

(51) Int. Cl.
*G08B 21/00* (2006.01)
*A61B 5/08* (2006.01)

(52) U.S. Cl. .................. 340/573.1; 340/665; 340/666; 5/615; 600/534

(58) Field of Classification Search .............. 340/573.1, 340/665–667, 573.4; 5/615, 654, 713, 722; 600/534, 595; 177/45, 144, 199
See application file for complete search history.

(56) References Cited

U.S. PATENT DOCUMENTS

| | | | |
|---|---|---|---|
| 779,576 A | 1/1905 | Berryman | 5/710 |
| 3,303,518 A | 2/1967 | Ingram | 5/710 |
| 3,772,717 A | 11/1973 | Yuen et al. | 5/422 |

(Continued)

FOREIGN PATENT DOCUMENTS

CA   2 393 880 A1   1/2004

(Continued)

OTHER PUBLICATIONS

The International Search Report and The Written Opinion for PCT/US06/26787, dated Mar. 6, 2008, (8 pages).

(Continued)

*Primary Examiner*—George A Bugg
*Assistant Examiner*—Anne V Lai
(74) *Attorney, Agent, or Firm*—Barnes & Thornburg LLP

(57) ABSTRACT

A lack of patient movement monitor and method. The monitor and method patient support includes a plurality of sensors located beneath a patient support to determine movement of a patient. An alarm is activated when patient movement over time is determined to be lacking.

21 Claims, 18 Drawing Sheets

U.S. PATENT DOCUMENTS

| | | | |
|---|---|---|---|
| 3,978,530 A | 9/1976 | Amarantos | 5/615 |
| 4,477,935 A | 10/1984 | Griffin | 5/241 |
| 4,483,029 A | 11/1984 | Paul | 5/689 |
| 4,525,885 A | 7/1985 | Hunt et al. | 5/713 |
| 4,527,298 A | 7/1985 | Moulton | 5/615 |
| 4,541,135 A | 9/1985 | Karpov | 5/710 |
| 4,637,083 A | 1/1987 | Goodwin | 5/689 |
| 4,638,519 A | 1/1987 | Hess | 5/713 |
| 4,825,486 A | 5/1989 | Kimura et al. | 5/713 |
| 4,839,512 A | 6/1989 | Speck | |
| 4,934,468 A | 6/1990 | Koerber, Sr. et al. | 177/144 |
| 4,944,060 A | 7/1990 | Peery et al. | 5/713 |
| 4,951,335 A | 8/1990 | Eady | 5/709 |
| 4,953,244 A | 9/1990 | Koerber, Sr. et al. | 5/600 |
| 4,993,920 A | 2/1991 | Harkleroad et al. | 417/44.2 |
| 5,020,176 A | 6/1991 | Dotson | 5/710 |
| 5,029,352 A | 7/1991 | Hargest et al. | 5/689 |
| 5,036,559 A | 8/1991 | Hargest | 5/689 |
| 5,060,174 A | 10/1991 | Gross | |
| 5,067,189 A | 11/1991 | Weedling et al. | 5/81.1 R |
| 5,117,518 A | 6/1992 | Schlid | |
| 5,121,512 A | 6/1992 | Kaufmann | 5/713 |
| 5,140,309 A | 8/1992 | Gusakov | 340/573.4 |
| 5,163,196 A | 11/1992 | Graebe et al. | 5/654 |
| 5,168,589 A | 12/1992 | Stroh et al. | 5/710 |
| 5,184,122 A | 2/1993 | Decious et al. | 340/870.16 |
| 5,267,364 A | 12/1993 | Volk | 5/713 |
| 5,269,030 A * | 12/1993 | Pahno et al. | 5/604 |
| 5,276,432 A | 1/1994 | Travis | 340/573.4 |
| 5,325,551 A | 7/1994 | Tappel et al. | 5/709 |
| 5,364,162 A | 11/1994 | Bar et al. | 297/284.8 |
| 5,483,709 A | 1/1996 | Foster et al. | 5/81.1 R |
| 5,483,711 A | 1/1996 | Hargest et al. | 5/725 |
| 5,539,942 A | 7/1996 | Melou | 5/655.3 |
| 5,542,136 A | 8/1996 | Tappel | 5/710 |
| 5,561,873 A | 10/1996 | Weedling | 5/713 |
| 5,561,875 A | 10/1996 | Graebe | 5/423 |
| 5,564,142 A | 10/1996 | Liu | 5/689 |
| 5,586,346 A | 12/1996 | Stacy et al. | 5/710 |
| 5,596,781 A | 1/1997 | Graebe | 5/710 |
| 5,611,096 A | 3/1997 | Bartlett et al. | 5/617 |
| 5,623,736 A | 4/1997 | Soltani et al. | 5/689 |
| 5,634,225 A | 6/1997 | Miller, Sr. et al. | 5/710 |
| D386,035 S | 11/1997 | Matsler et al. | D6/601 |
| 5,684,460 A * | 11/1997 | Scanlon | 340/573.1 |
| 5,689,845 A | 11/1997 | Sobieralski | 5/654 |
| 5,699,570 A | 12/1997 | Wilkinson et al. | 5/713 |
| 5,787,531 A | 8/1998 | Pepe | 5/710 |
| 5,794,288 A | 8/1998 | Soltani et al. | 5/713 |
| 5,815,864 A | 10/1998 | Sloop | 5/654 |
| 5,815,865 A | 10/1998 | Washburn et al. | 5/713 |
| 5,829,081 A | 11/1998 | Pearce | 5/654 |
| 5,845,352 A | 12/1998 | Matsler et al. | 5/654 |
| 5,873,137 A | 2/1999 | Yavets-Chen | 5/713 |
| D407,353 S | 3/1999 | Bar et al. | D12/133 |
| D408,767 S | 4/1999 | Bar et al. | D12/133 |
| 5,917,180 A | 6/1999 | Reimer et al. | 250/227.14 |
| D412,685 S | 8/1999 | Bar et al. | D12/133 |
| D413,085 S | 8/1999 | Bar et al. | D12/133 |
| D413,841 S | 9/1999 | Bar et al. | D12/133 |
| 5,954,402 A | 9/1999 | McInturff | 297/440.22 |
| D415,567 S | 10/1999 | Bar | D24/165 |
| D415,834 S | 10/1999 | Bar | D24/165 |
| 5,970,789 A | 10/1999 | Meyer et al. | |
| D416,326 S | 11/1999 | Bar | D24/165 |
| 5,984,418 A | 11/1999 | McInturff | 297/440.24 |
| 6,014,346 A | 1/2000 | Malone | 368/10 |
| 6,095,611 A | 8/2000 | Bar et al. | 297/440.21 |
| 6,145,142 A | 11/2000 | Rechin et al. | 5/706 |
| 6,165,142 A | 12/2000 | Bar | 600/595 |
| D439,098 S | 3/2001 | Matsler et al. | D6/601 |
| 6,212,718 B1 | 4/2001 | Stolpmann et al. | |
| 6,280,392 B1 * | 8/2001 | Yoshimi et al. | 600/534 |
| D463,701 S | 10/2002 | Gorcherding et al. | D6/601 |
| 6,474,743 B1 | 11/2002 | Harker et al. | 297/440.21 |
| 6,487,739 B1 | 12/2002 | Harker | 5/726 |
| 6,560,804 B2 | 5/2003 | Wise et al. | 5/713 |
| 6,564,410 B2 | 5/2003 | Graebe et al. | 5/710 |
| 6,593,588 B1 | 7/2003 | Reimer | |
| 6,623,080 B2 | 9/2003 | Clapper | 297/452.41 |
| 6,646,556 B1 * | 11/2003 | Smith et al. | 340/573.1 |
| 6,687,936 B2 | 2/2004 | Graebe et al. | 5/710 |
| 6,687,937 B2 | 2/2004 | Harker | 5/726 |
| 6,701,556 B2 | 3/2004 | Romano et al. | 5/653 |
| 6,848,135 B1 | 2/2005 | Kohlman | 5/713 |
| 6,877,178 B2 | 4/2005 | Chapman et al. | 5/713 |
| 6,892,405 B1 * | 5/2005 | Dimitriu et al. | 5/615 |
| 6,987,232 B2 * | 1/2006 | Smith et al. | 200/85 R |
| 7,145,461 B2 * | 12/2006 | Lehrman et al. | 340/573.1 |
| 7,253,366 B2 * | 8/2007 | Bhai | 177/45 |
| 2001/0011480 A1 | 8/2001 | Reimer | |
| 2002/0066143 A1 | 6/2002 | Graebe et al. | 5/710 |
| 2003/0030319 A1 | 2/2003 | Clapper | 297/452.41 |
| 2005/0172398 A1 * | 8/2005 | Smith et al. | 5/81.1 R |
| 2006/0152378 A1 * | 7/2006 | Lokhorst et al. | 340/666 |

FOREIGN PATENT DOCUMENTS

| | | |
|---|---|---|
| DE | 103 16 162 A1 | 10/2004 |
| DE | 103 33 742 A1 | 2/2005 |
| EP | 853 918 A2 | 7/1998 |
| FR | 2814062 | 3/2002 |
| GB | 159299 | 2/1921 |
| GB | 2 092 439 A | 8/1982 |
| GB | 2 199 803 A | 7/1988 |
| WO | WO 94/09686 | 5/1984 |
| WO | WO 95/31920 | 11/1995 |
| WO | WO 96/33641 | 10/1996 |
| WO | WO 2004/006768 | 1/2004 |
| WO | WO 2005/013878 | 2/2005 |

OTHER PUBLICATIONS

Renaissance™, Therapeutic Mattress Replacement System, Pegasus Airwave Inc., date unknown.

A Hill-Rom solution, ACUCAIRE Continuous Airflow System, Date Unknown.

Air Flow 5000 Mattress Replacement System, Atlantis Medical, Milltown, NJ, date unknown.

Apropos, CRS-8500, National Patient Care Systems, date unknown.

ASAP II Therapy System, DynaMedics Corporation, London, ON, Canada, Mar. 1995.

Bazooka, Innovative Medical System, Manchester, NH, 1995.

DFS® Homecare Advanced Dynamic Flotation System, HNE Healthcare, Manalapan, NJ, date unknown.

Economic Relief, Bio Therapy® Plus, Sunrise Medical Bio Clinic, Ontario, CA, date unknown.

First Step, Mattress Replacement System, KCI, San Antonio, TX, 1991.

GAYMAR Sof-Care Plus © CompanionÔ System, Gaymar Industries, Inc., 1994.

Hill-Rom PrimeAire ARS Pressure Relief Mattress, Date Unknown.

Impression, Pressure Relief Therapy, KCI, date unknown.

Lumex AkroTech 4000, Lumex, date unknown.

microAirÔ 1000, GSI Medical Systems, Carmel, NY, 1989.

Pro 2000 MRS, Pneu-Care Series, Cardio Systems, Dallas, TX, date unknown.

Prodigy Mattress Crown Theraputics, Inc. Date Unknown.
Roho Dry Flotation Isolette see roho.com/medical/isolette.jsp Date Unknown.
Roho series Crown Theraputic, Inc. See woundheal.com Date Unknown.

Tytex Group AirX #D Spacer Fabric see tytex.cms.digitalis.dk Date Unknown.

* cited by examiner

LACK OF PATIENT MOVEMENT MONITOR AND METHOD

CROSS-REFERENCE TO RELATED APPLICATIONS

This application claims the benefit of U.S. Provisional Patent Application Ser. No. 60/567,215 to Balaton et al., entitled PRESSURE RELIEF SUPPORT SURFACE, filed Apr. 30,2004, and U.S. Provisional Patent Application Ser. No. 60/665,241 of Hopkins et al., entitled THERMOREGU-LATING DEVICE, filed Mar. 25, 2005, and U.S. Provisional Patent Application Ser. No. 60/665,141 of Hopkins et al., entitled THERMOREGULATING DEVICE, filed Mar. 25, 2005, and U.S. Provisional Patent Application Ser. No. 60/636,252 of Chambers et al., entitled QUICK CONNECTOR FOR MULTIMEDIA, filed Dec. 15, 2004, and U.S. Provisional Patent Application Ser. No. 60/608,013 of Branson, entitled ROTATION SENSOR FOR A MATTRESS, filed Sep. 8, 2004, all of which are under obligation to be assigned to the assignee of the present invention, and all of which are incorporated herein by this reference in their entirety.

The present application is also related to U.S. patent application Ser. No. 11/120,080, entitled PATIENT SUPPORT, U.S. patent application Ser. No. 11/119,980, entitled PRESSURE RELIEF SURFACE, and U.S. patent application Ser. No. 11/119,991, entitled PATIENT SUPPORT HAVING REAL TIME PRESSURE CONTROL, all of which are filed on May 2, 2005, are under obligation to be assigned to the assignee of the present invention, and are incorporated herein by this reference.

In addition, PCT patent application Publication No. WO 2005/104904, entitled BODY SUPPORT APPARATUS HAVING AUTOMATIC PRESSURE CONTROL AND RELATED METHODS of Lokhorst et al filed on May 2, 2005, is incorporated herein in its entirety.

BACKGROUND

The present invention relates to a device for supporting a patient, such as a mattress. In particular, the present invention relates to patient supports appropriate for use in hospitals, acute care facilities, and other patient care environments. Further, the present invention relates to pressure relief support surfaces and support surfaces that are configured to accommodate and operate with a variety of sizes and styles of beds, bed frames, and patient types.

Known patient supports are disclosed in, for example, U.S. Pat. No. 5,630,238 to Weismiller et al., U.S. Pat. No. 5,715, 548 to Weismiller et al., U.S. Pat. No. 6,076,208 to Heimbrock et al., U.S. Pat. No. 6,240,584 to Perez et al., U.S. Pat. No. 6,320,510 to Menkedick et al., U.S. Pat. No. 6,378,152 to Washburn et al., and U.S. Pat. No. 6,499,167 to Ellis et al., all of which are owned by the assignee of the present invention and all of which are incorporated herein by this reference.

SUMMARY

In accordance with one aspect of the present invention, a method is provided for a pressure adjustable support, including a bladder assembly having a plurality of bladders to support a patient, a plurality of sensors, each of the plurality of sensors subtending at least one of the vertical bladders to sense a force transmitted through the bladders. The method includes the steps of: setting a time period for determining an activity level, setting a threshold level with respect to the sensed force, sampling the forces sensed by each of the plurality of sensors transmitted through the bladders; and generating a signal as a function of the set time period, the set threshold level, and the sampled forces.

In another aspect of the present invention there is provided a motion monitor device for monitoring the motion of a patient lying on a hospital bed, including a mattress. The motion monitor includes a plurality of sensors subtending the mattress, and a user interface device, operatively coupled to the plurality of sensors, the user interface device including a screen to display motion information and an input device to input motion parameters to determine patient motion.

BRIEF DESCRIPTION OF THE DRAWINGS

Aspects of the present invention are more particularly described below with reference to the following figures, which illustrate an exemplary embodiment of the present invention.

DETAILED DESCRIPTION

Figure 1:
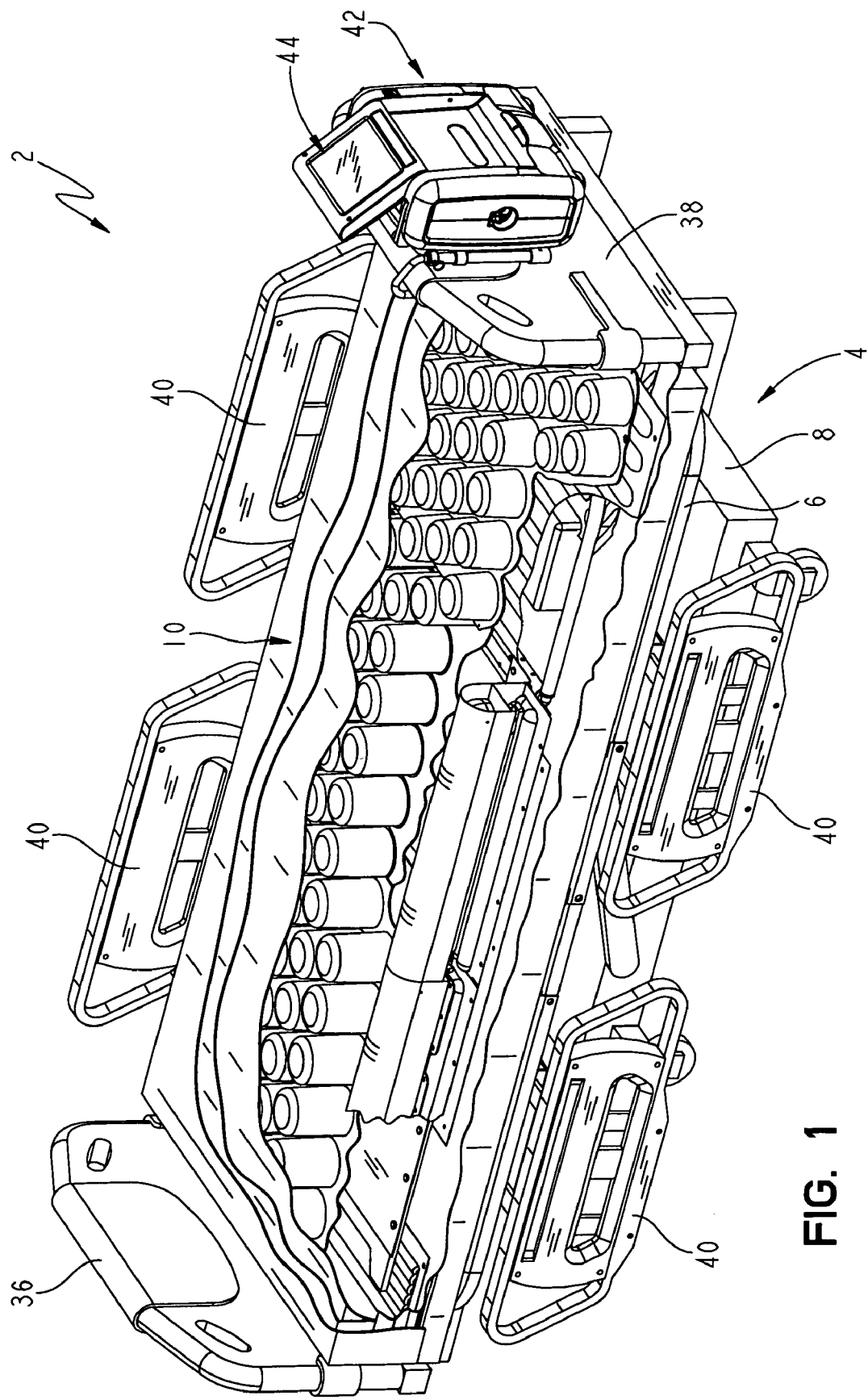
FIG. 1 is a perspective view of a patient support positioned on an exemplary hospital bed, with a portion of the patient support being cut away to show interior components of the patient support.

FIG. 1 shows an embodiment of a patient support 10 in accordance with the present invention. Patient support 10 is positioned on an exemplary bed 2. Bed 2, as illustrated, is a hospital bed including a frame 4, a headboard 36, a footboard 38, and a plurality of siderails 40.

Frame 4 of the exemplary bed 2 generally includes a deck 6 supported by a base 8. Deck 6 includes one or more deck sections (not shown), some or all of which may be articulating sections, i.e., pivotable with respect to base 8. In general, patient support 10 is configured to be supported by deck 6.

Patient support 10 has an associated control unit 42, which controls inflation and deflation of certain internal components of patient support 10. Control unit 42 includes a user interface 44, which enables caregivers and service providers to configure patient support 10 according to the needs of a particular patient. For example, support characteristics of patient support 10 may be adjusted according to the size, weight, position, or activity of the patient.

User interface 44 also enables patient support 10 to be adapted to different bed configurations. For example, deck 6 may be a flat deck or a step deck. A caregiver may select the appropriate deck configuration via user interface 44.

Figure 2:
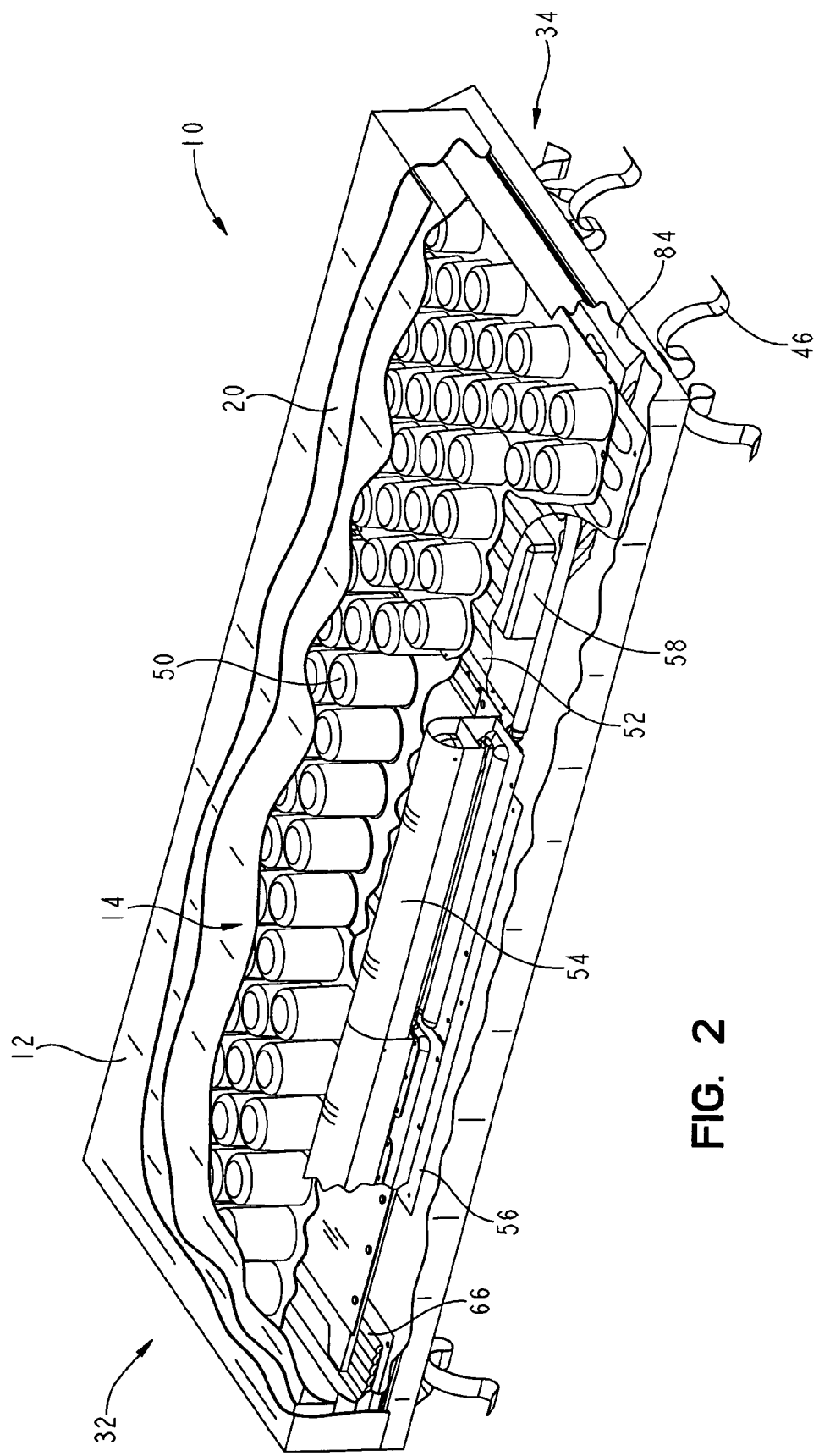
FIG. 2 is a perspective view of a patient support, with a portion being cut away to show interior components of the patient support.

Referring now to FIG. 2, patient support 10 has a head end 32 configured to support a patient's head and upper body region, and a foot end 34 configured to support a patient's feet and lower body region. Patient support 10 includes a cover 12 which defines an interior region 14. In the illustrated embodiment, interior region 14 includes a first layer 20, a second layer 50, and a third layer 52.

As shown in FIG. 2, first layer 20 includes a three-dimensional material, second layer 50 includes a plurality of vertically-oriented air bladders located underneath the first layer, and third layer 52 includes a plurality of pressure sensors located underneath the vertical bladders of second layer 50, as more particularly described below.

Also located within interior region 14 are a plurality of bolsters 54, a plurality of filler portions 56, and a pneumatic valve control box 58. A fire-resistant material (not shown) may also be included in the interior region 14.

Patient support 10 may be coupled to deck 6 by one or more couplers 46. Illustratively, couplers are conventional woven straps including a Velcro® brand or similar fastener. However, it is understood that other suitable couplers may be used.

Figure 3:
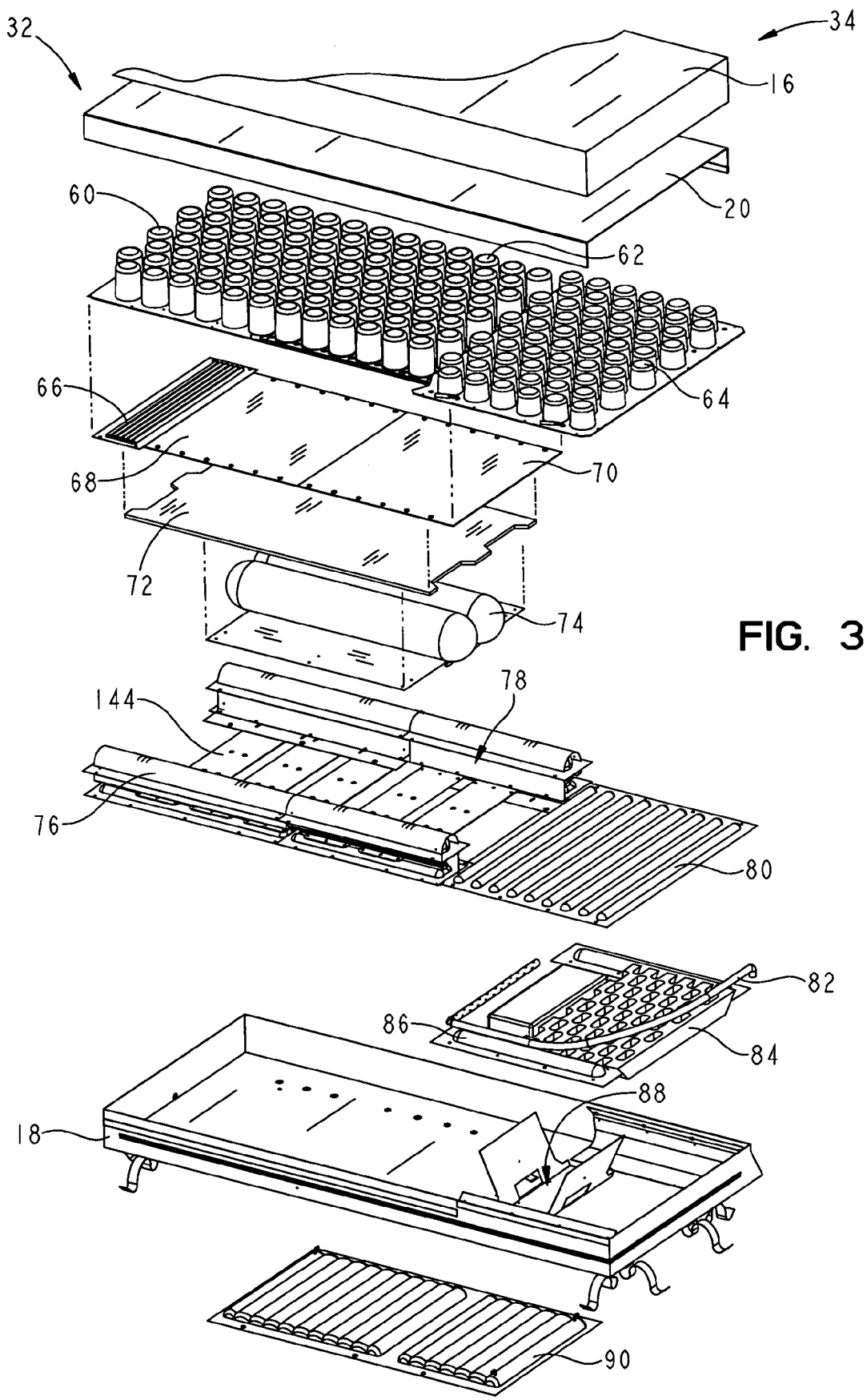
FIG. 3 is an exploded view of components of a patient support.

Components of one embodiment of a patient support in accordance with the present invention are shown in exploded view in FIG. 3. This embodiment of patient support 10 includes a top cover portion 16 and a bottom cover portion 18. Top cover portion 16 and bottom cover portion 18 couple together by conventional means (such as zipper, Velcro®, snaps, buttons, or other suitable faster) to form cover 12, which defines interior region 14. While a plurality of layers and/or components are illustrated within interior region 14, it will be understood by those of skill in the art that the present invention does not necessarily require all of the illustrated components.

A first support layer 20 is located below top cover portion 16 in interior region 14. Support layer includes one or more materials, structures, or fabrics suitable for supporting a patient, such as foam, inflatable bladders, or three-dimensional material. Suitable three-dimensional materials include Spacenet® and/or Tytex™-brand or similar materials.

A second support layer including one or more bladder assemblies, is located underneath the first support layer 20. The illustrated embodiment of the second support layer includes first, second and third bladder assemblies, namely, a head section bladder assembly 60, a seat section bladder assembly 62, and a foot section bladder assembly 64. However, it will be understood by those skilled in the art that other embodiments include only one bladder assembly extending from head end 32 to foot end 34, or other arrangements of multiple bladder assemblies, for example, including an additional thigh section bladder assembly.

A pressure-sensing layer illustratively including first and second sensor pads, namely a head sensor pad 68 and a seat sensor pad 70, is positioned underneath bladder assemblies 60, 62, 64. Head sensor pad 68 is generally aligned underneath head section bladder assembly 60, and seat sensor pad 70 is generally aligned underneath seat section bladder assembly 62, as shown. It will be understood by those skilled in the art that other embodiments include a single sensor pad or additional sensor pads, for example, located underneath foot section bladder assembly 64, and/or different alignments of the sensor pads.

In the illustrated embodiment, a turn-assist cushion 74 is located below sensor pads 68, 70. The exemplary turn-assist cushion 74 shown in FIG. 3 includes a pair of inflatable bladders. Suitable turn-assist cushions are disclosed in, for example, U.S. Pat. No. 6,499,167 to Ellis, et al., which patent is owned by the assignee of the present invention and incorporated herein by this reference. One of ordinary skill in the art will readily appreciate that turn-assist cushions 74 are not necessarily a required element of the present invention.

A plurality of other support components 66, 72, 76, 78, 80, 84, 86, 90 are also provided in the illustrated embodiment of FIG. 3. One or more of these support components are provided to enable patient support 10 to be used in connection with a variety of different bed frames, in particular, a variety of bed frames having different deck configurations. One or more of these support components may be selectively added to or removed from patient support 10 in order to conform patient support 10 to a particular deck configuration, such as a step or recessed deck or a flat deck.

The support components illustrated in FIG. 3 are made of foam, inflatable bladders, three-dimensional material, other suitable support material, or a combination of these. For example, as illustrated, head filler 66 includes a plurality of foam ribs extending transversely across patient support 10. Filler portion 72 includes a foam layer positioned substantially underneath the sensor pads 68, 70 and extending transversely across the patient support 10.

Head bolster assembly 76 and seat bolster assembly 78 each include longitudinally-oriented inflatable bladders spaced apart by coupler plates 144.

As illustrated, first foot filler portion 80 includes a plurality of inflatable bladders extending transversely across patient support 10, and second foot filler portion 84 includes a foam member, illustratively with portions cut out to allow for retractability or for other reasons. Deck filler portion 90 includes a plurality of transversely-extending inflatable bladders. As illustrated, deck filler portion 90 includes two bladder sections, and is located outside of cover 12. However, one of ordinary skill in the art will recognize that deck filler portion 90 may include one or more bladder regions, or may be located within interior region 14, without departing from the scope of the present invention.

Also provided in the illustrated embodiment are a pneumatic valve box 58 and an air supply tube assembly 82. Receptacle 88 is sized to house pneumatic valve box 58. In the illustrated embodiment, receptacle 88 is coupled to bottom cover portion 18.

Figure 4A:
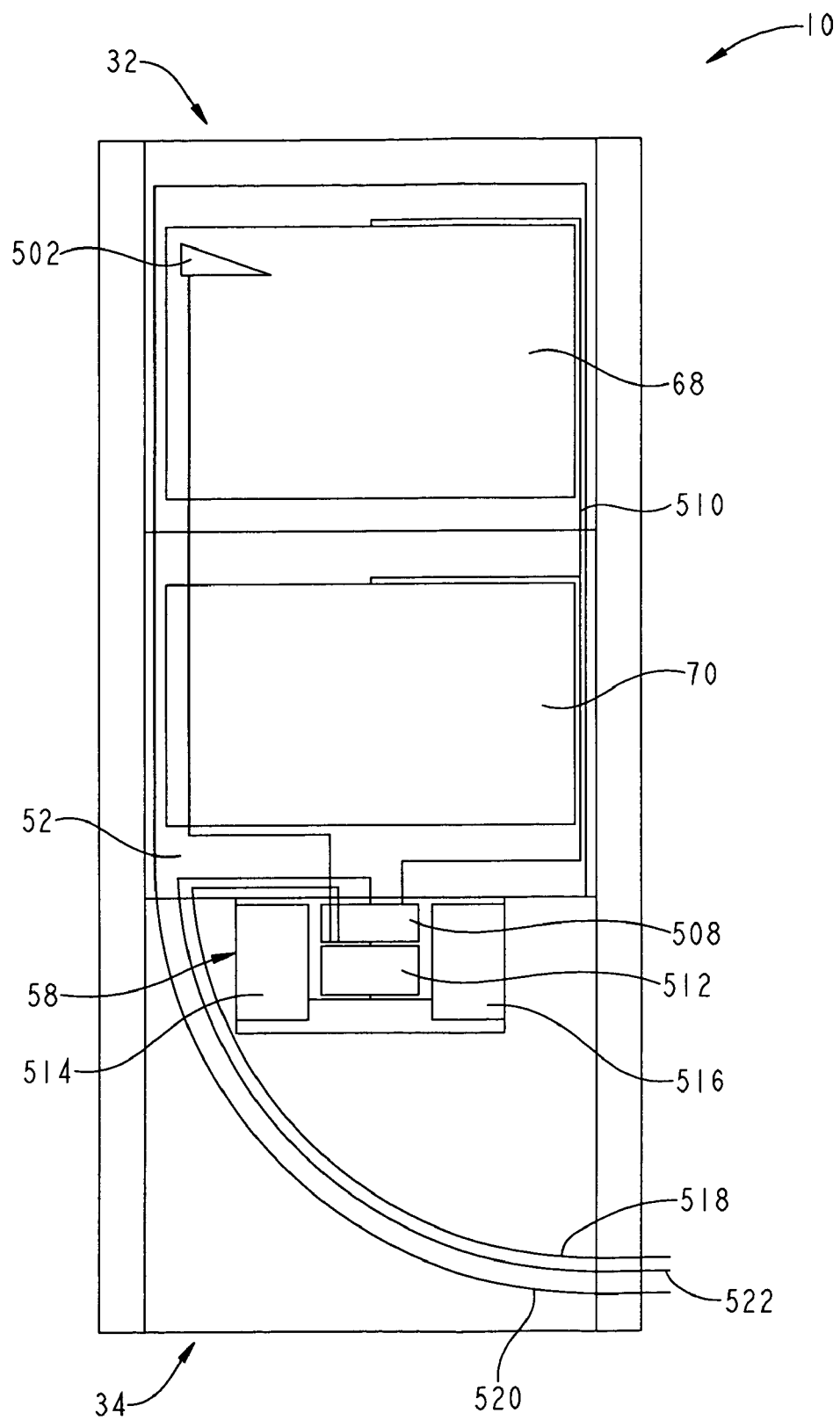
FIGS. 4A and 4B are a simplified schematic diagram of the control system and the mattress assembly of the present invention.
Figure 4B:
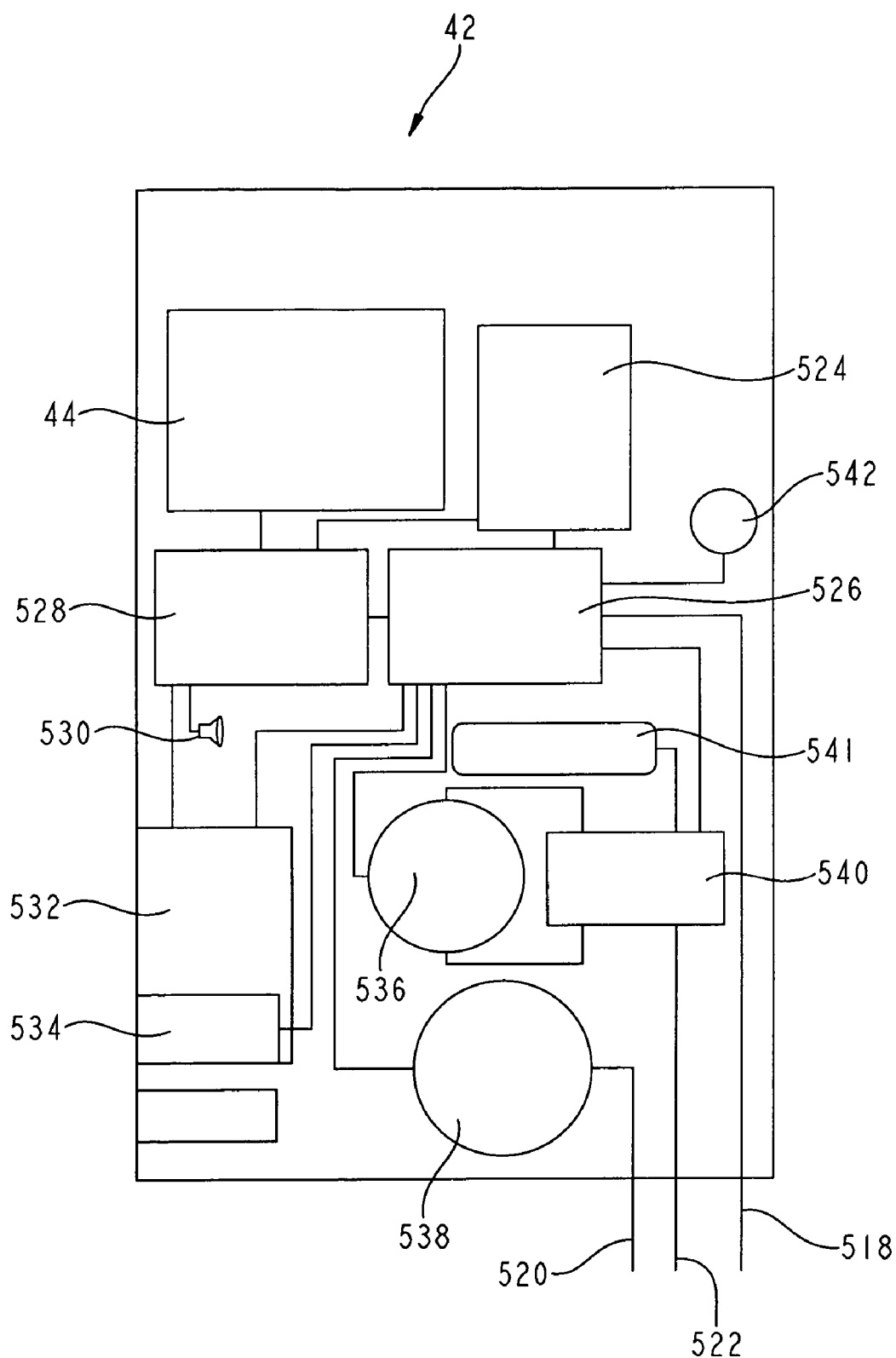

FIGS. 4A and 4B are a simplified schematic diagram of a control system and the patient support or mattress 10 of the present invention. FIG. 4A illustrates the patient support 10 including the various components of patient support 10 whereas FIG. 4B illustrates the control unit 42 and the various components. The patient support 10 includes the sensor pad 52 which is coupled to the pneumatic valve control box 58 as previously described. The sensor pad 52 includes a head sensor pad 68 and a seat sensor pad 70. The head sensor pad 68 is located at the head end 32 of the mattress 10. The seat sensor pad 70 is located at a middle portion of the mattress 10 which is located between the head end 32 and a location of the pneumatic valve control box 58. The seat sensor pad 70 is located such that a patient laying upon the mattress 10 may have its middle portion or seat portion located thereon when in a reclined state. In addition, when the head end 32 of the mattress 10 is elevated, the seat portion of the patient is located upon the seat sensor pad 70. As previously described with respect to FIG. 3, the head sensor pad 68 is located beneath the head section bladder assembly 60 and the seat sensor pad 70 is located beneath the seat section bladder assembly 62. Each one of the sensors of the head sensor pad 68 or the seat sensor pad 70 is located beneath one of the upstanding cylindrical bladders or cushions. A head angle sensor 502 is coupled to the control box 58 where signals received from the sensor 52 may provide head angle information and pressure adjustment information for pressure in the seat bladders 62.

The sensor pad 52 includes individual sensors, integrated electronics, and cabling to be described later herein in more detail. The sensor pad 52 is coupled through the associated cabling to the pneumatic control box 58. The pneumatic control box includes a multiplexer 508 coupled to the head sensor pad 68 and the seat sensor pad 70 through a signal and control line 510. The multiplexer board 508 is also coupled to an air control board 512 which is in turn coupled to a first valve block 514 and a second valve block 516. A communication/power line 518 is coupled to the control unit 42 of FIG. 4B. Likewise, a ventilation supply line 520 which provides for air flow through the patient support 10 for cooling as well as removing moisture from the patient is also coupled to the control unit 42 of FIG. 4B. An air pressure/vacuum supply line 522 is coupled to the control unit 42 as well.

The control unit 42 of FIG. 4B, also illustrated in FIG. 1, includes the display 44, which displays user interface screens, and a user interface input device 524 for inputting to the control unit 42 user selectable information, such as the selection of various functions or features of the present device. The selections made on the user interface input device 524 control the operation of the patient support 10, which can include selectable pressure control of various bladders within the mattress 10, control of the deck 6, for instance to put the bed 2 in a head elevated position, as well as displaying the current state of the mattress, deck position, and other features.

An algorithm control board 526 is coupled to the user interface input device 524. The algorithm control board 526 receives user generated input signals received through the input device 524 upon the selection of such functions by the user. The input device 524 can include a variety of input devices, such as pressure activated push buttons, a touch screen, as well as voice activated or other device selectable inputs. The algorithm control board 526 upon receipt of the various control signals through the user input device 524 controls not only the operation of the mattress 10 but also a variety of other devices which are incorporated into the control unit 42. For instance, the algorithm control board 526 is coupled to a display board 528 which sends signals to the display 44 to which it is coupled. The display board 528 is also connected to a speaker 530 which generates audible signals which might indicate the selection of various features at the input device 24. The algorithm control board 526 receives the required power from power supply 532 which includes an AC input module 534, typically coupled to a wall outlet within a hospital room.

The algorithm control board 526 is coupled to a compressor 536 and a blower 538. Both the compressor 536 and the blower 538 receive control signals generated by the algorithm control board 526. The compressor 536 is used to inflate the air bladders. The blower 538 is used for air circulation which is provided through the ventilation supply line 520 to the mattress 10. It is, however, possible that the compressor 536 may be used to both inflate the bladders and to circulate the air within the mattress 10. A pressure/vacuum switch valve 540 is coupled to the compressor 536 which is switched to provide for the application of air pressure or a vacuum to the mattress 10. A muffler 541 is coupled to the valve 540. In the pressure position, air pressure is applied to the mattress 10 to inflate the mattress for support of the patient. In the vacuum position, the valve 540 is used to apply a vacuum to the bladders therein such that the mattress may be placed in a collapsed state for moving to another location or to deflate bladders during turn assist. A CPR button 542 is coupled to the algorithm control board 526.

As illustrated, the algorithm control board 526, the compressor 536, the blower 538, and the user input device or user control module 524 are located externally to the mattress and are a part of the control unit 42 located on the footboard 38. The sensors and sensor pad 52, the pneumatic valve control box 58, and the air control board or microprocessor 512 for controlling the valves and the sensor pad system 52 are located within the mattress 10. It is within the present scope of the invention to locate some of these devices within different sections of the overall system, for instance, such that the algorithm control board 526 could be located within the mattress 10 or the air control board 512 could be located within the control unit 42.

Figure 5:
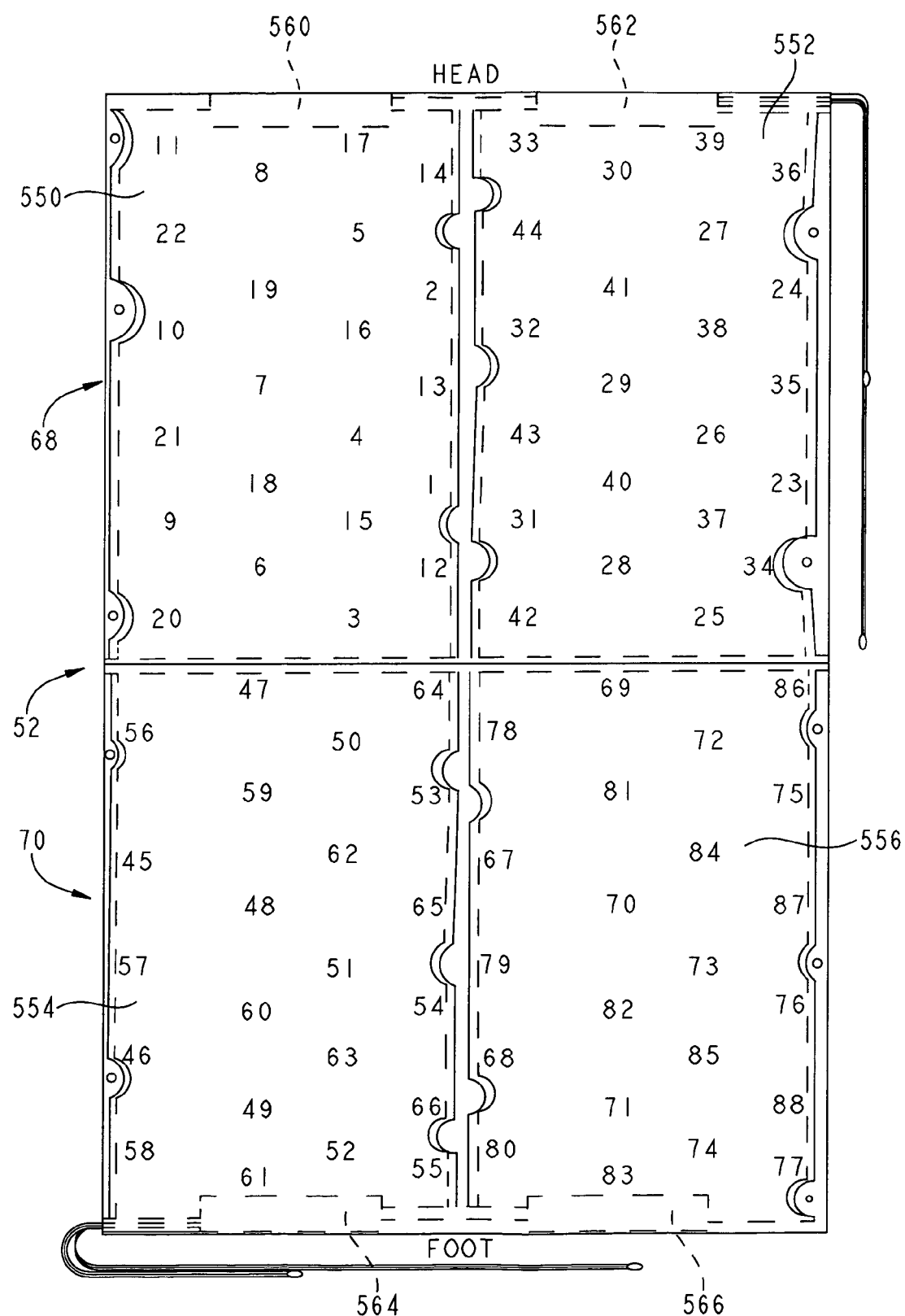
FIG. 5 illustrates a first and second sensor pad including a sequence of reading data from the sensors of the sensor pad.

FIG. 5 illustrates the sensor pad 52 including the head sensor pad 68 and the seat sensor pad 70. Each of the pads includes a plurality of sensors configured to provide a reflected wave energy signal is described in PCT Publication WO 2004/00678A1 having a publication date of 22 Jan. 2004, the disclosure of which is incorporated by reference herein. The sensor pads include fiber pairs which introduce wave energy, typically light, into a compressible medium such as foam. The light introduced to the foam is scattered in a manner dependent on the force applied to the surface of the foam. The reflected or scattered light energy is detected and converted to an electrical signal indicative of the force applied to the sensor. Both the head sensor pad 68 and seat sensor pad 70 each include 44 individual sensors spaced throughout. The location of each of individual pressure sensing elements is indicated by a number 1 through 88. The sensor pad 68 and the sensor pad 70 each include and can be considered as a collection of 44 independent interface pressure sensors. The areas in between sensors are generally not sensitive to pressure.

The head sensor pad 68 includes a first sensor group 550 and a second sensor group 552. The first sensor group 550 is located in an upper left quadrant of the sensor pad 52 whereas the second sensor group 552 is in an upper right quadrant of the sensor pad 52. Each of the individual sensor groups 550 and 552 include 22 sensors, the location of which is indicated and identified by a number. For instance, the first sensor group 550 includes sensors 1 through 22 and the second sensor group 552 includes sensors 23 through 44. The numerical order of the individual sensors indicates the sequence in which the information from each of these sensors is accessed by the multiplexer board 508.

The seat sensor pad 70 includes a third sensor group 554 and a fourth sensor group 556 configured to be substantially the same as the first sensor group 550 and the second sensor group 552 as previously described. Each of the sensor groups includes 22 sensors which have numbers indicating the sequence in which the signal information is accessed or derived therefrom.

Each of the sensor groups 550, 552, 554, and 556 include an optical system device 560, 562, 564, and 566 respectively. Each of these devices includes a cable for connection to the pneumatic valve control box 58. Since each of the first sensor group 550, 552, 554, and 556 are substantially identical in construction, the optical system device 560 will be described and its description will apply to the remaining optical system devices 562, 564 and 566.

The optical system device 560 is an opto-electronics interface board including software embedded on a micro controller integrated with an opto-board and the sensor pad itself. The embedded software of the microprocessor is typically referred to as "firmware". As described in PCT publication WO 2004/006768A1, each of the sensors includes fiber optic cable which is coupled to the opto-electric board. Two light emitting diodes supply light to each of the individual sensors and a single photo diode array reads the optical inputs of all 22 sensors within a sensor group. An erasable programmable read only memory and a serial interface driver for communication are included. The primary purpose of the optical system device is to acquire the information sensed by each of the individual sensors which result from the reflected light which has been passed through the fiber optic cable to the individual sensor. Algorithms within the embedded microprocessor are used to linearize the data sensed by the sensors. The sensor data and diagnostic data are made available to the multiplexer 508 through RS-232 ports. Data is transmitted though the network 578, which may be a controller area network (CAN) bus, to the algorithm control unit 526.

Figure 6:
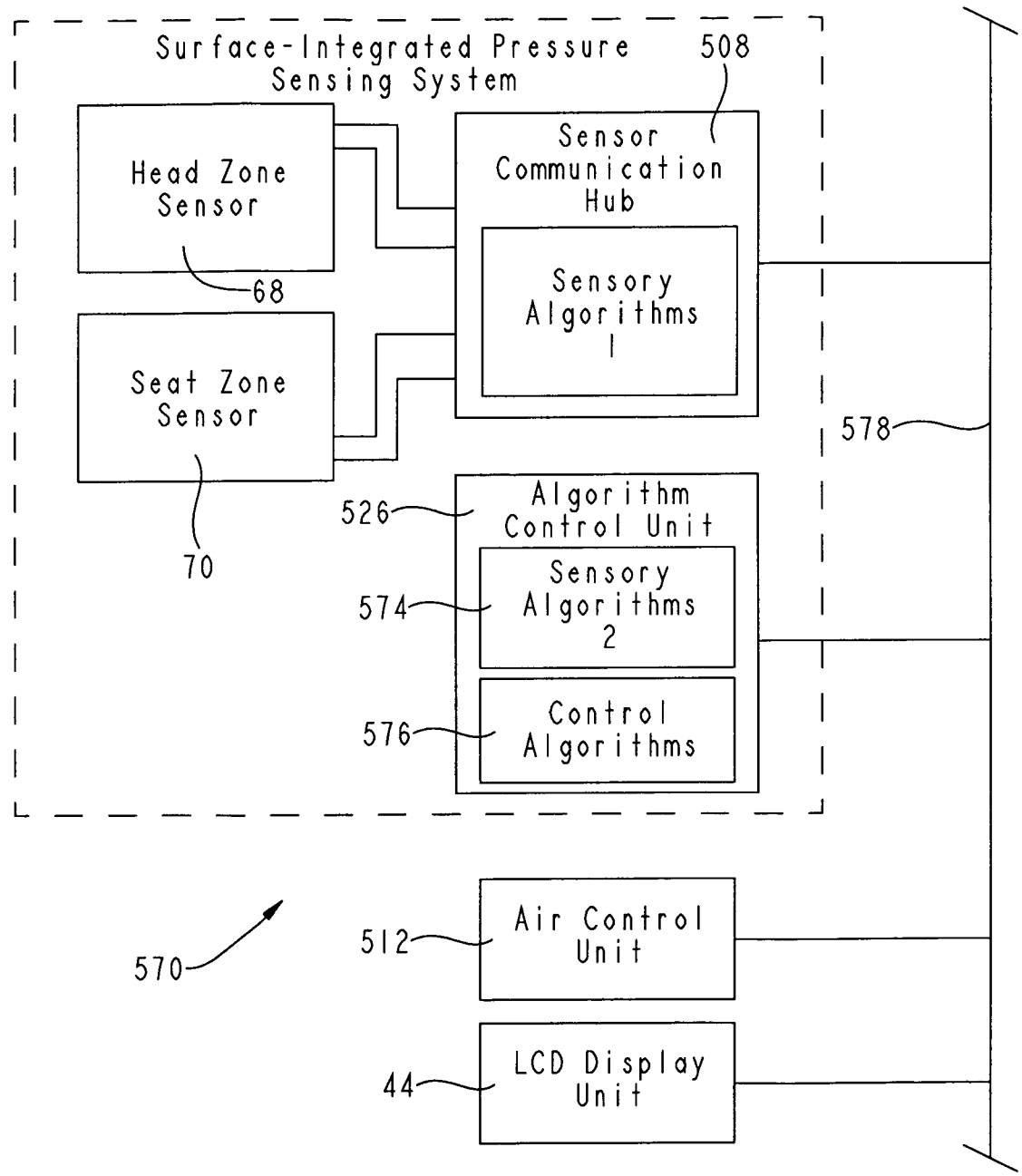
FIG. 6 illustrates a functional block diagram illustrating the head zone and seat zone sensors and other system components coupled to a communication network.

FIG. 6 illustrates an overall system architecture 570 of the present invention. As previously described, the multiplexer board 508, also known as a sensor communication hub, is coupled to the head zone sensor 68 and the seat zone sensor 70. The multiplexer 508 as well as the optical system devices includes a number of sensory algorithms to be described later herein. Also included in the system architecture 570 is the algorithm control unit 526 which includes a second set of sensory algorithms 574 and control algorithms 576. The output of the multiplexer 508 and the algorithm control unit 526 are coupled to a network 578 which is also coupled to the air control unit 512 and the LCD display unit 44. The network 578 includes interface hardware, also known as a communication hub. The network 578 acts as the communication bus for the various hardware, software, and firmware control devices.

As previously described, the multiplexer 508 includes the sensory algorithms 572. The algorithm control unit 526 also includes sensory algorithms which may include algorithms for providing pressure relief, for providing a motion metric, for providing weight estimation, and for providing information to a LCD module which includes a calculation of statistics model.

Figure 7:
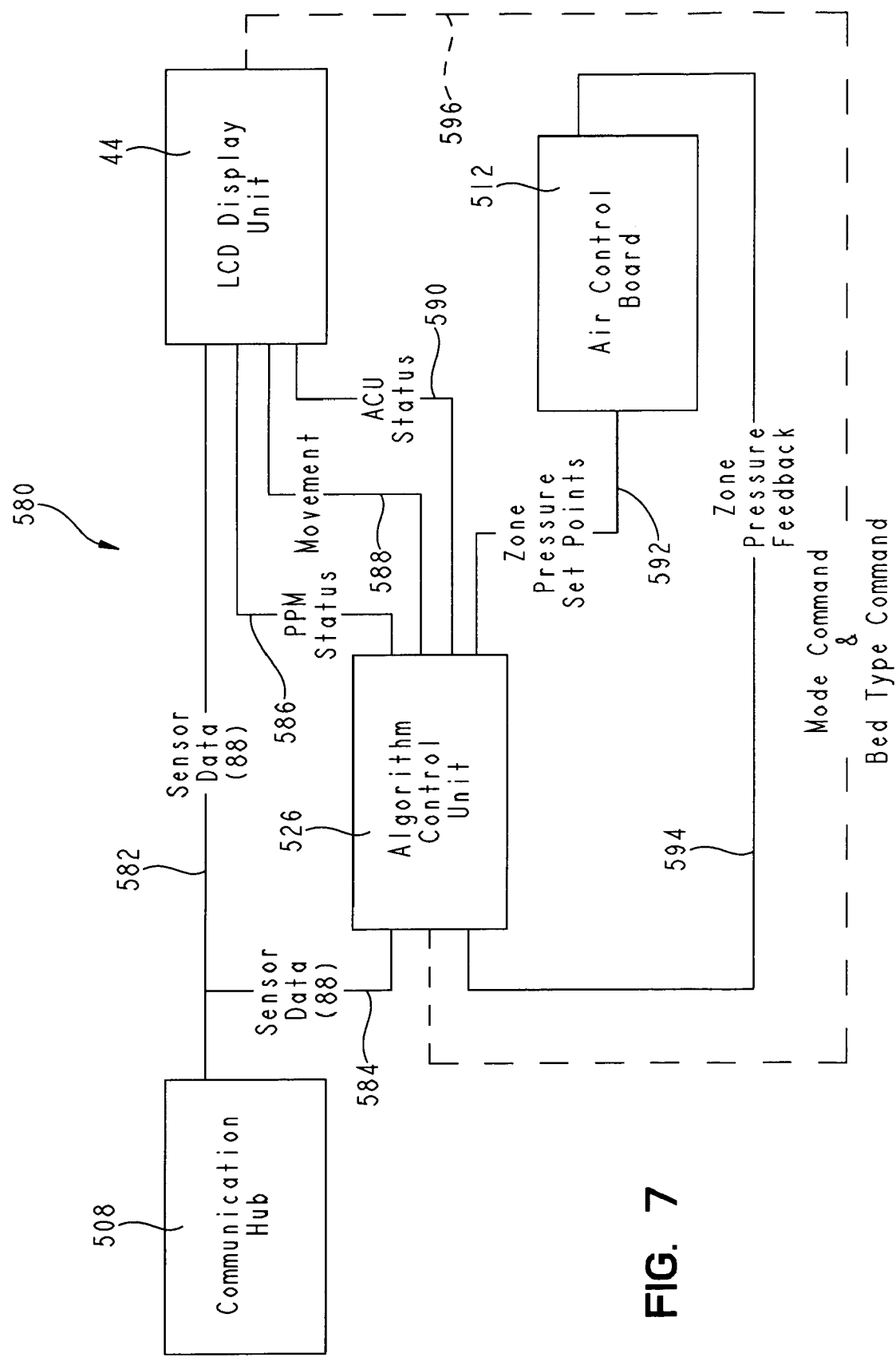
FIG. 7 illustrates a block diagram for a control system of the present invention including an algorithm control unit.

FIG. 7 illustrates a block diagram of a control system 580 incorporating the LCD display unit 44, the air control board 512, the communication hub or network 508, and the algorithm control unit 526. The communication hub 508 which receives sensor data from the head zone sensor 68 and the seat zone sensor 70 is coupled to both the LCD display unit 44 and the algorithm control unit 526 through a first sensor data line 582 and a second sensor data line 584 respectively. As described with respect to FIG. 6, the algorithm control unit 526 includes sensory algorithms 574 and control algorithms 576. The algorithm control unit 526 includes a first output line 586 coupled to the LCD display unit 44 for transmitting patient position monitor status, a second control line 588 for communicating movement status, and a third control line 590 for communicating the status of the algorithm control unit. In addition, the algorithm control unit 526 includes a fourth output line 592 which transmits the zone pressure set points for each of the head, seat and foot zones to the air control board 512 to which the line 592 is coupled. The air control board 512, which includes the pressure sensors previously described, sends control pressure zone feedback signals through a line 594 back to the algorithm control unit 526. The LCD display unit 44 through the user input interface device 524 also sends control signals to the algorithm control unit 526 through a control line 596 which includes signals such as various mode command signals as well as bed type command signals for adjusting the frame or deck of the bed.

As previously described in FIG. 6, the present invention includes sensory algorithms as well as control algorithms. The sensory algorithms are provided in firmware located within the multiplexer 508 and the algorithm control unit 526. Sensory algorithms include the following: bottom out detection, where a portion of the subject is supported by the bed frame as opposed to the surface, bed exit detection, sitting on the side of a bed detection, detection of a patient lying on the edge of the surface, detecting a lack of patient movement on the surface over a period of time, providing patient position monitoring by distinguishing between the following six positions left lying, left sitting, center lying, center sitting, right lying, right sitting, and measuring patient weight within plus or minus 20% within the bed and the flat position. The control system algorithms which are located in the control system algorithm firmware 576 optimize pressure reduction by dynamic load distribution adjustment of the surface air bladders of the mattress 10 located above the head sensor pad 68 and the seats sensor pad 70.

As described with respect to FIG. 7, the algorithm control unit 526 is coupled to the LCD Display Unit 44 through the second control line 588 for communicating movement status. Movement status is monitored according to the sensor data which is received over the line 584 by the algorithm control unit 526 as previously described. The movement status is used to determine patient motion or patient movement which is displayed on the LCD Display Unit 44 and which includes screen displays for a motion monitor to be described herein.

Figure 8:
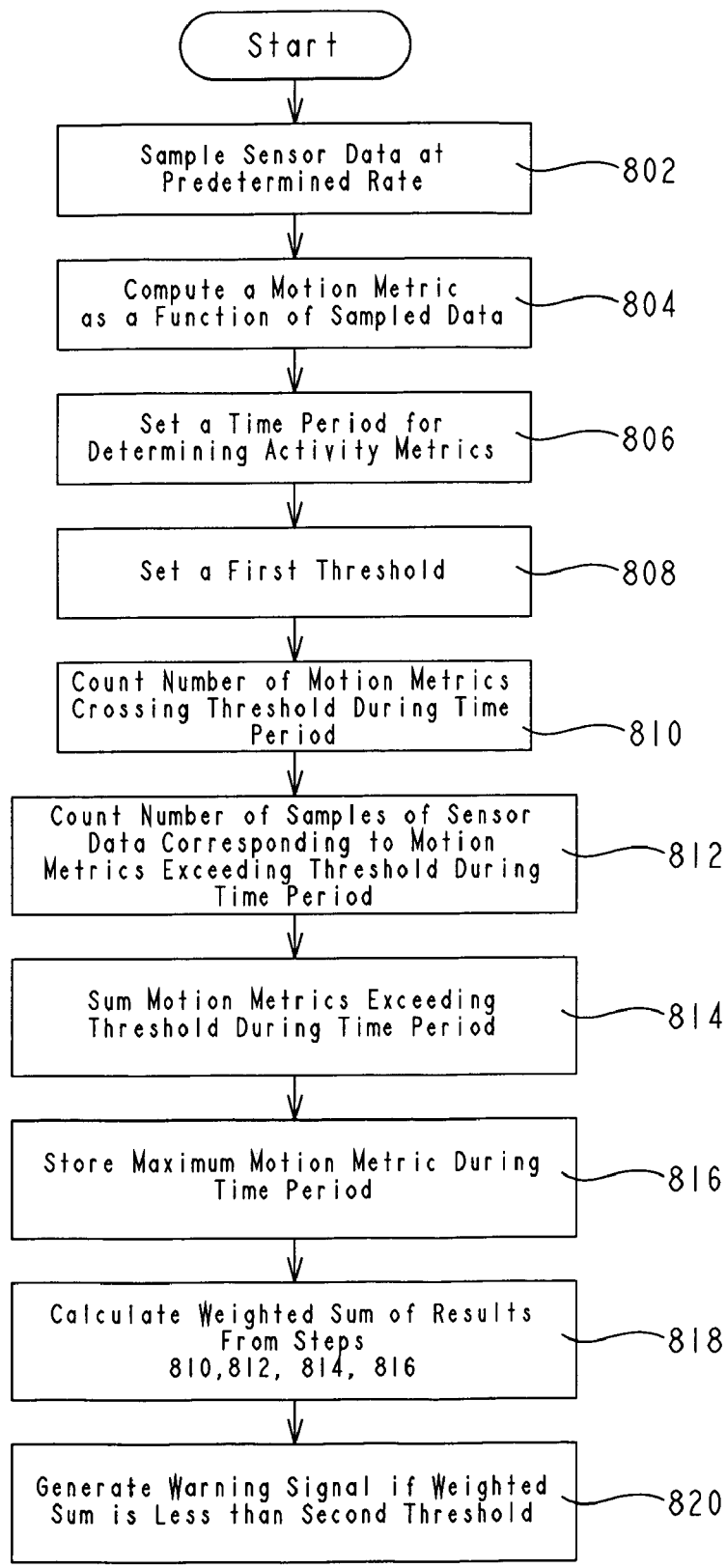
FIG. 8 is a flow diagram illustrating one embodiment of the present invention to determine patient movement with the patient movement monitor.

FIG. 8 is a flow diagram for a motion monitor of the present invention. The flow diagram 800 of FIG. 8 provides the steps embodied in the algorithm and firmware of the present invention. To provide patient movement or motion status for use by a caregiver, the sensor data is sampled at a pre-determined rate from each of the plurality of the sensors of the sensor pad 70. The sensors are sampled at a rate of four hertz at step 802. Due to the large amount of information provided at the sampling rate of four hertz, it has been found that this data received by the algorithm control unit 526 may be transformed into numbers of metrics which provide an accurate indication of patient movement. At step 804, a motion metric is computed as a function of the sampled data. While it is within the scope of the present invention to take a time derivative of the sum of all of the sensor outputs, or to sum the squared time derivative of the individual sensor outputs, or to sum the absolute value of the time derivative of the individual sensor outputs, the flowchart describes summing the absolute values of the individual high pass filtered sensor outputs to arrive at the motion metric. This motion metric is also called an instantaneous motion metric which may determined according to the following equation:

$$m = \frac{1}{N}\sum_{i=1}^{N}|h(t_i)|$$

$T_i$ is the i-th sensor value where "N" is the number of sensors, and the function H is a (temporal) high pass filter. At step 806, a time period is selected for determining activity metrics at later steps. In addition, a first threshold is set at Step 808 to be described in more detail.

At step 810, a first activity metric is determined in which the number of motion metrics that cross the threshold during the time period is counted. This is called a "zero-crossings" count. At Step 812, a second activity metric is determined in which the number of samples of sensor data corresponding to the motion metrics exceeding the threshold during the set time period is calculated. This activity metric is called "time-over zero". At Step 814, a third activity metric is determined where the amount of the motion metrics which exceed the first threshold during the pre-set time period is summed together. At Step 816, a fourth motion metric is determined where the maximum motion metric which occurs during the time period is stored. Each of the activity metrics determined at Steps 810, 812, 814, and 816 can be represented as a single value which occurs during the set time period established at Step 806. Each of these activity metrics are then combined into a single value at Step 818 by computing a weighted sum of the four activity metrics. Coefficients used in the weighted sum are selected in a manner that differentiates a patient's motion of interest. In this manner, the magnitude of movement of a patient over the pre-determined time period may be compressed into a single value. Once this value is determined at Step 818, it may be compared to a second threshold. If the weighted sum is less than the second threshold, then a warning signal may be transmitted over the line 588 to the LCD Display Unit 44.

Figure 9:
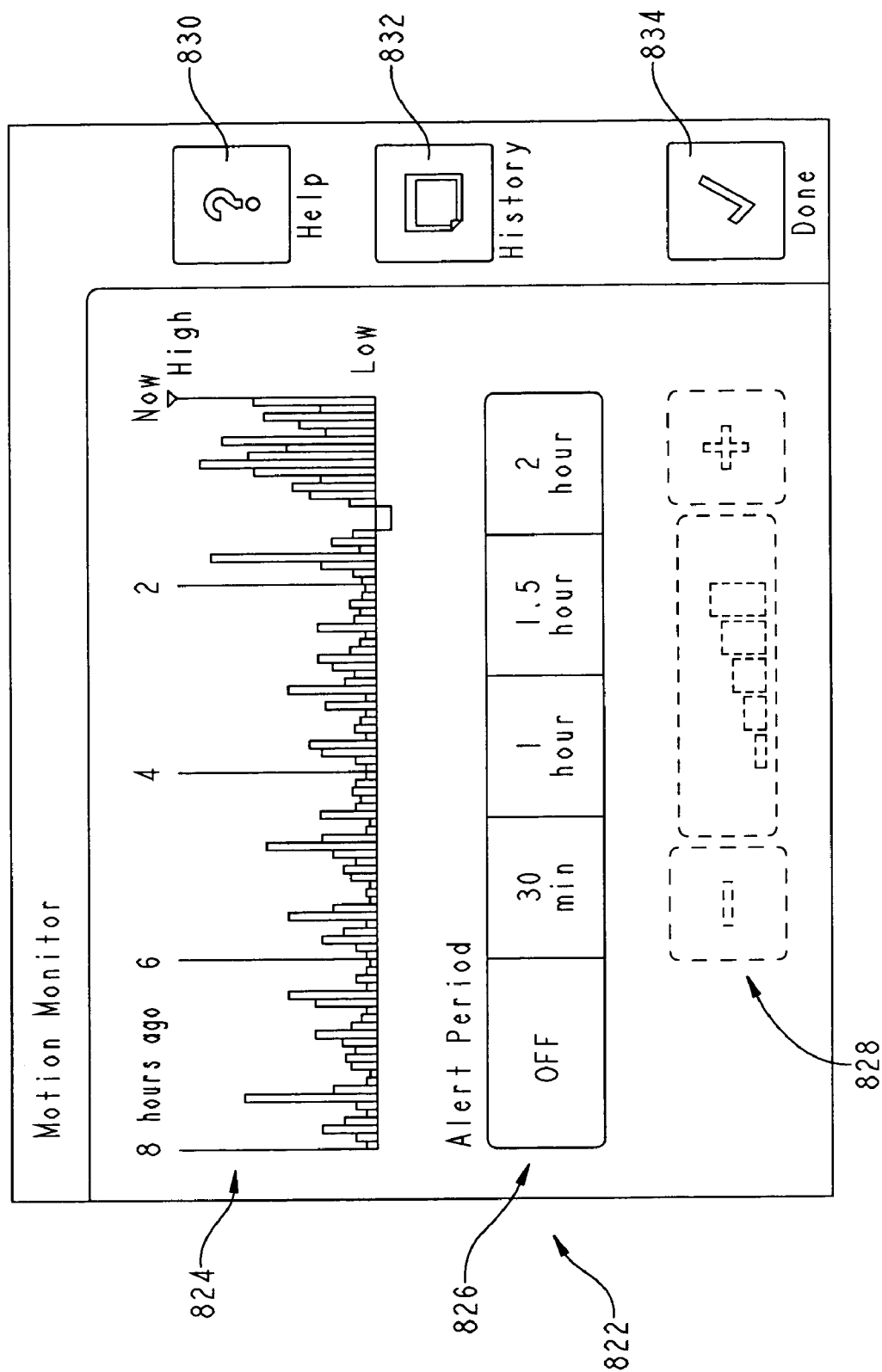
FIG. 9 is a screen display of a motion monitor user interface screen when the motion monitor is in the off condition.

FIG. 9 is a screen display of a motion monitor user interface screen of the present invention. The interface screen 822 includes a first display portion to display the weighted sums in a graphical user interface. A second display portion 826 includes a number of user interface buttons for adjusting the time period over which a patient's motion is monitored. These buttons may include a touch screen display or other user input devices. As illustrated, the monitored time periods may be selected as 30 minutes, 1 hour, 1.5 hours and 2 hours, as well as an off position. A third display portion 828, here shown in dotted outline, enables a user or a caregiver to adjust the second threshold level as described in Step 820 of FIG. 8. The third display portion may be displayed as a lighter shade or as a background image when the monitor is in the off position. In addition, the user interface 822 includes a help button 830 to provide instructions for a user or caregiver, a history button 832 to be described later, and a done or complete button in which the caregiver can move to a different set of user interface screens.

Figure 10:
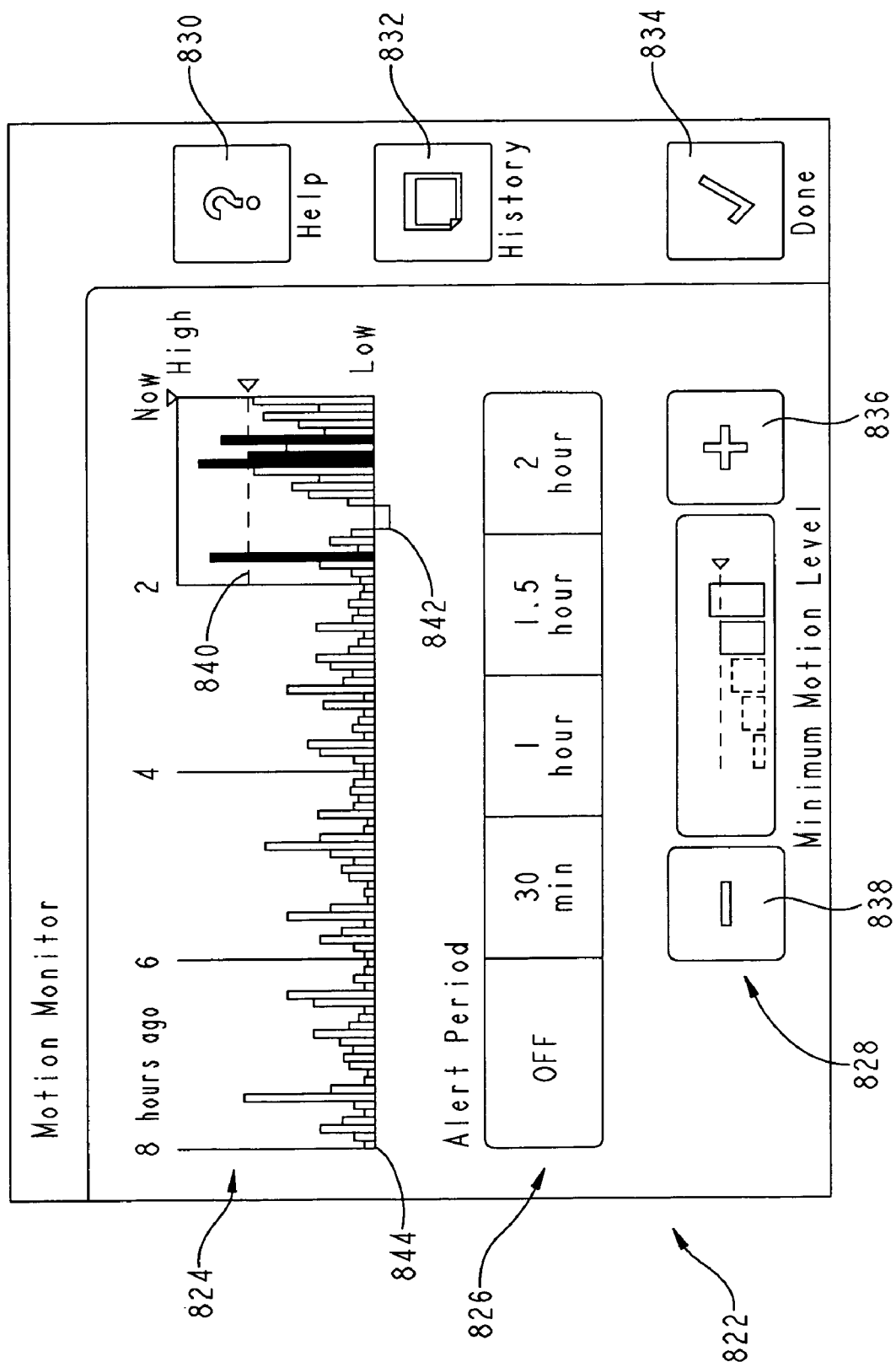
FIG. 10 is a screen display of the motion monitor user interface screen when the motion monitor is set to a time period of two hours.

As illustrated in FIG. 10, the caregiver may select from one of five threshold levels in the third display portion 828. When an alert period is selected, the third display portion 828 is visually enhanced to indicate an alert period has been selected. The selected threshold level, also shown here as a minimum motion level, establishes a minimum activity level which the caregiver selects to monitor the patient's activity level. As shown, a plus button 836 allows the caregiver to increase the second threshold or minimum motion level and a minus button 838 allows the caregiver to reduce the second threshold or minimum motion level. If the activity level of the patient stays below the set threshold during the selected alarm period, an audible and a visual alarm may activate or sound. A bar chart in the first display portion 824 is updated every 5 minutes. This 5 minutes of activity corresponds to the time period selected for determining activity metrics as determined in Step 806 of FIG. 8. Other time periods are within the scope of the present invention. Each bar of the portion 824 is shown to be 5 minutes wide.

Each of the vertical bars of the first display portion 824 corresponds to one of the five minute time periods. A threshold level line 840 is displayed to indicate the minimum motion level set by the buttons 836 or 838. When it is determined that the minimum motion level exceeds the threshold 840, the bars of the bar chart are highlighted to indicate that the minimum motion level has been exceeded. While the bars of the bar chart exceeding the level 840 are illustrated as shaded bars, it is within the scope of the present invention to shade the bars with different levels of gray or to color code the individual bars for use with a color display. The bar chart also indicates when the bed is empty with a bar 842 which extends below a low line 844. Bed empty is determined by the sensors having sensed a lack of patient weight or force.

Every 30 minutes, a calculation is made to determine if any of the 5 minute bars have surpassed the caregiver selected minimum motion level. While these threshold calculations are performed every 30 minutes, an alarm is only activated at the end of the caregiver selected alert period as illustrated at the second portion 826. For example, if a period of 2 hours (120 minutes) is selected as the time period, calculations may be made before an alarm occurs at the end of the 2 hour time period. If each of the four calculations, one for each 30 minute time period, determines that the threshold has not been surpassed, an alarm will sound. However, if the threshold has been surpassed during any of the four periods, then no alarm will sound and the motion monitor will continue to record and calculate data. Correspondingly, the 1 hour and 1.5 hour alarm periods require respectively two and three consecutive 30 minute calculations with the threshold not being exceeded to cause an alarm.

If the threshold is not exceeded as described, a visual and audible alarm signals to the caregiver that the patient should be attended to. The caregiver attending to the patient cancels the alarm. The pre-set time period will then start again. During this new period, patient activity will continue to be monitored and displayed on the screen. If the threshold has been surpassed, indicating that the patient is moving, then the motion monitor continues to acquire data in 5 minute increments and threshold calculations at the end of each 30 minute period are performed to determine an alarm condition.

Figure 11:
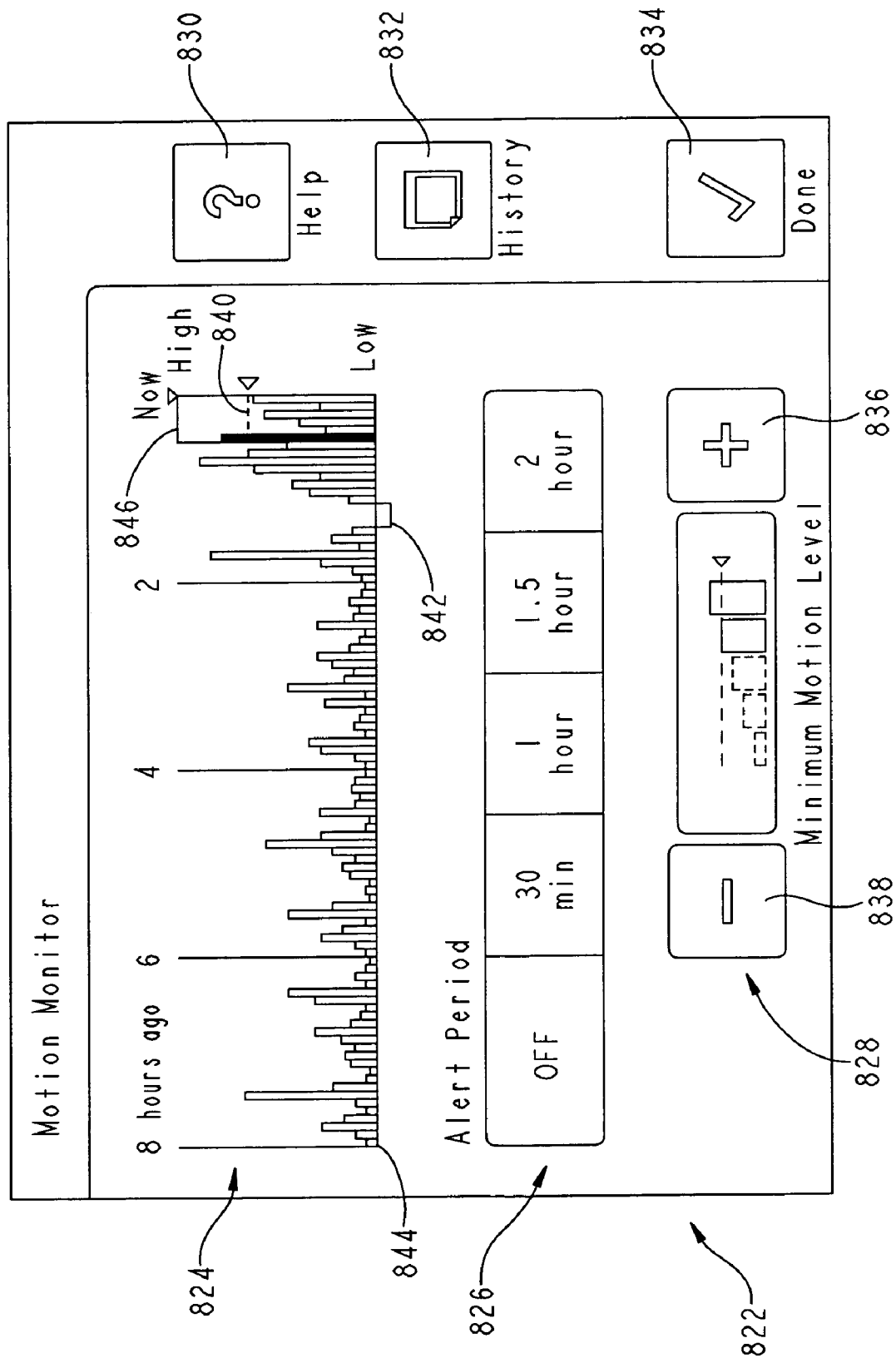
FIG. 11 is a screen display of the motion monitor user interface screen when the motion monitor is set to a time period of 30 minutes and the minimum motion level is set to a level of 4 out of 5.

FIG. 11 is a screen display 822 of the motion monitor user interface screen when the motion monitor is set to a time period of 30 minutes. As can be seen in FIG. 11, the caregiver would adjust the alert period by pressing the 30 minute button such that the bar chart or graphical display located in the first portion 824 indicates that a monitoring period of 30 minutes has been selected. The monitoring period of 30 minutes is defined by the user interface to include a rectangular portion 846 which encompasses or surrounds the bars within the 30 minute time period. This section, while indicated with lines, may also be indicated by using background colors such that the background color of the 6 bars making up the 30 minute time period may be displayed with a background of a different color than the bars. This rectangular portion may also be seen in FIG. 10. As before, if any of the individual bars within the 30 minute time period exceed the set motion level, the bars are indicated as a shaded bar.

Figure 12:
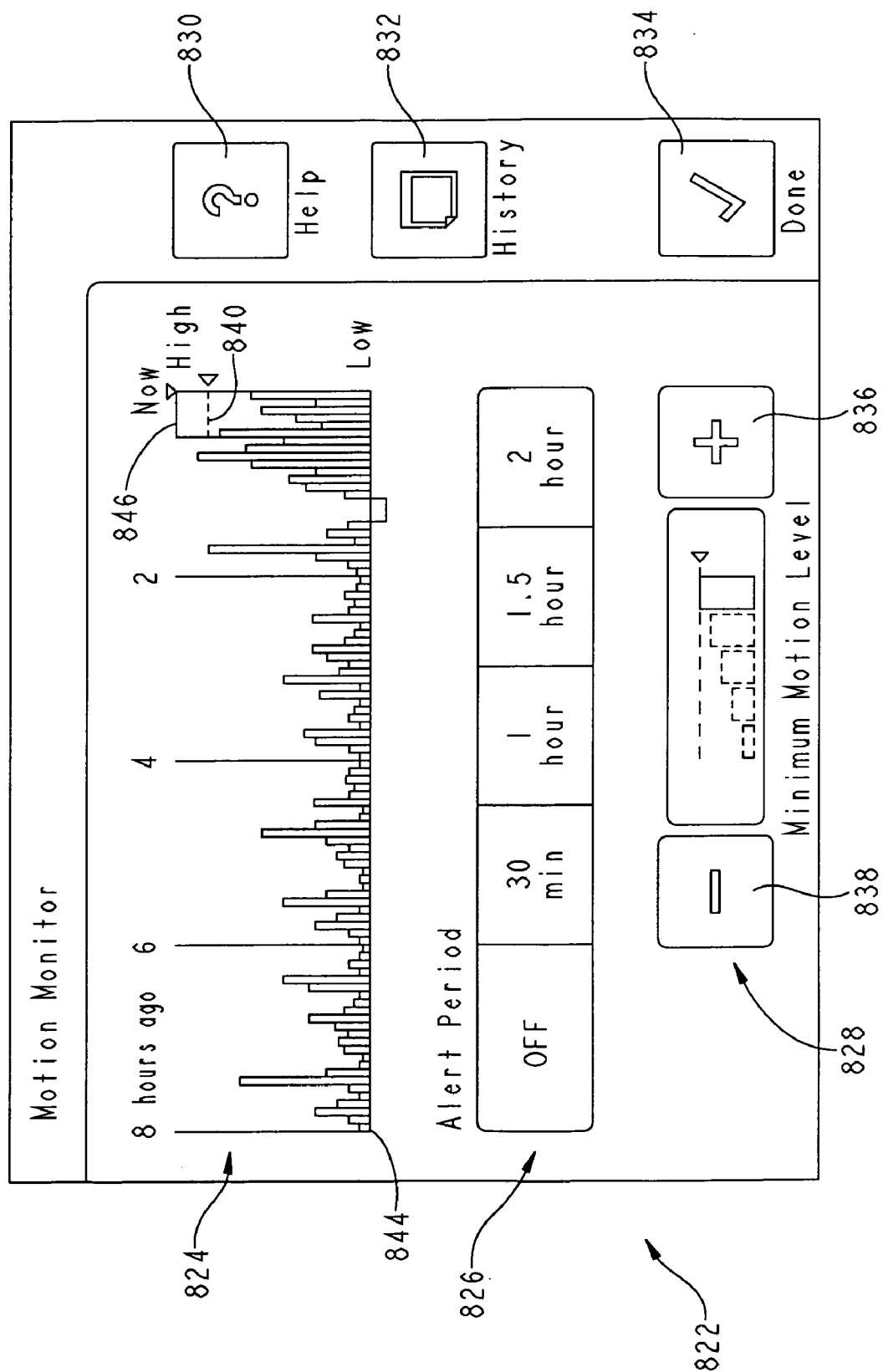
FIG. 12 is a screen display of the motion monitor user interface screen when the motion monitor is set to a time period of 30 minutes and the minimum motion level is set to the highest setting.

FIG. 12 is a screen display of the motion monitor user interface when the motion monitor time period is set to 30 minutes and the minimum motion level is set to the highest setting. In this illustration, none of the individual bars exceeds the set threshold level 840 during the 30 minute time period. Consequently, none of the bars have been highlighted to indicate that the threshold level has been exceeded. In this situation where none of the bars have exceeded the minimum set motion level, an alarm would sound to indicate to the caregiver that the minimum motion level has not been reached.

Figure 13:
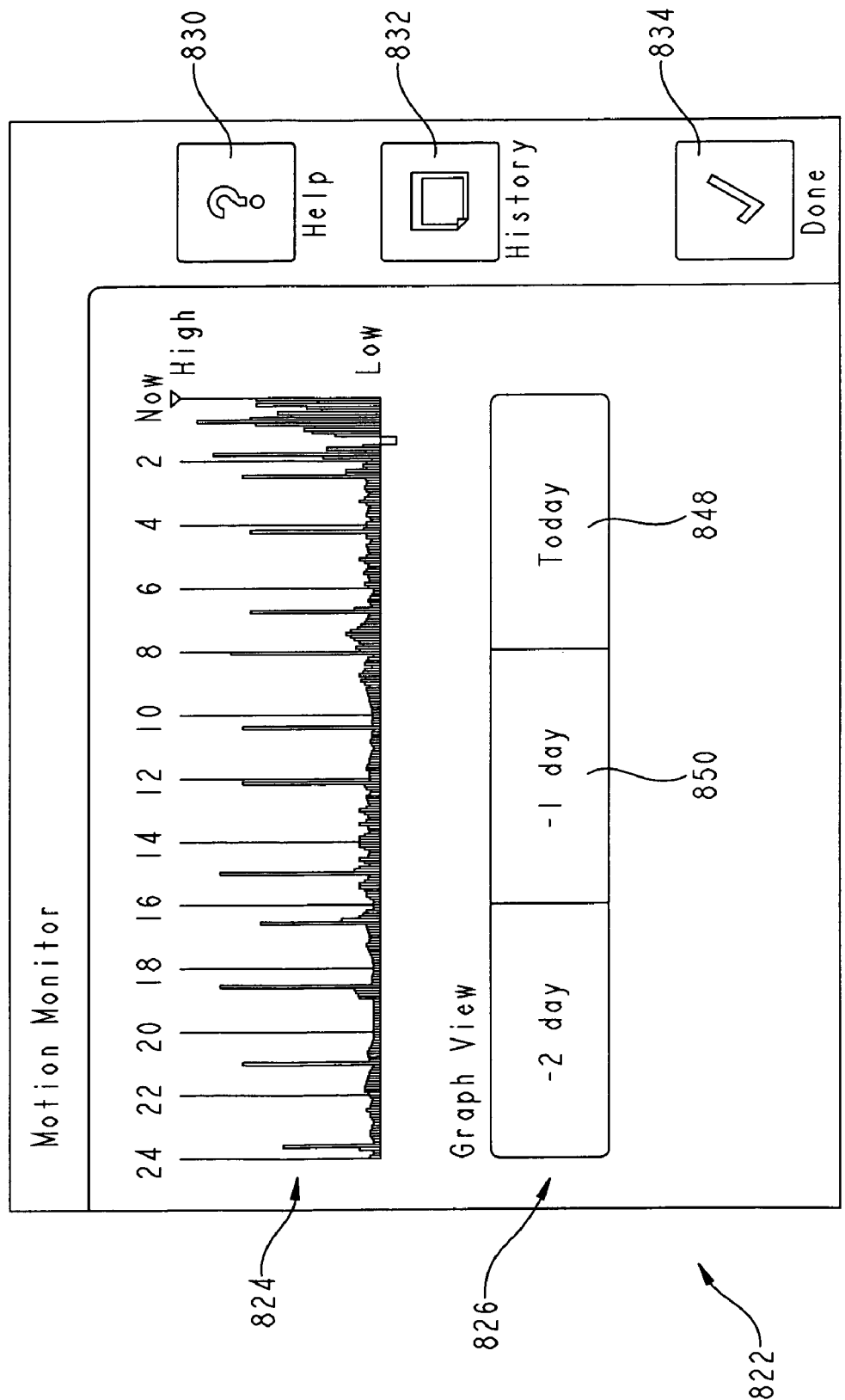
FIG. 13 is a screen display of the motion monitor user interface screen when the history button is selected to display a default history view showing the past 24 hours of monitored motion.

FIG. 13 is a screen display of the motion monitor user interface screen 822 when the history button 832 is selected to display a default history view showing the previous 24 hours of monitored motion. Other periods of default history, such as the previous 8 hours may also be selected and displayed. To view the history profile, which is displayed in the first section 824, the caregiver presses the history button 832 upon which the bar chart of the section 824 is displayed. Since the default condition is a representation of the motion for the last 24 hours, a 24 hour bar chart is displayed with each of the individual bars for the entire time period being displayed. In addition to the amount of the patient's activity level, the time patient activity occurs during the day can also be tracked. This information may be used by a caregiver to make care decisions for the patient. In addition to displaying a period of the previous 24 hours by pushing a Today button 848, the previous days activity level may be viewed by pressing a minus one day button 850. Pressing the minus one day button displays a period of 24 hours beginning 24 hours prior to the current time and ending 48 hours prior. Likewise, pushing the minus 2 day button displays a time period beginning 48 hours prior to the current time and extending for 24 hours prior to that start time.

Figure 14:
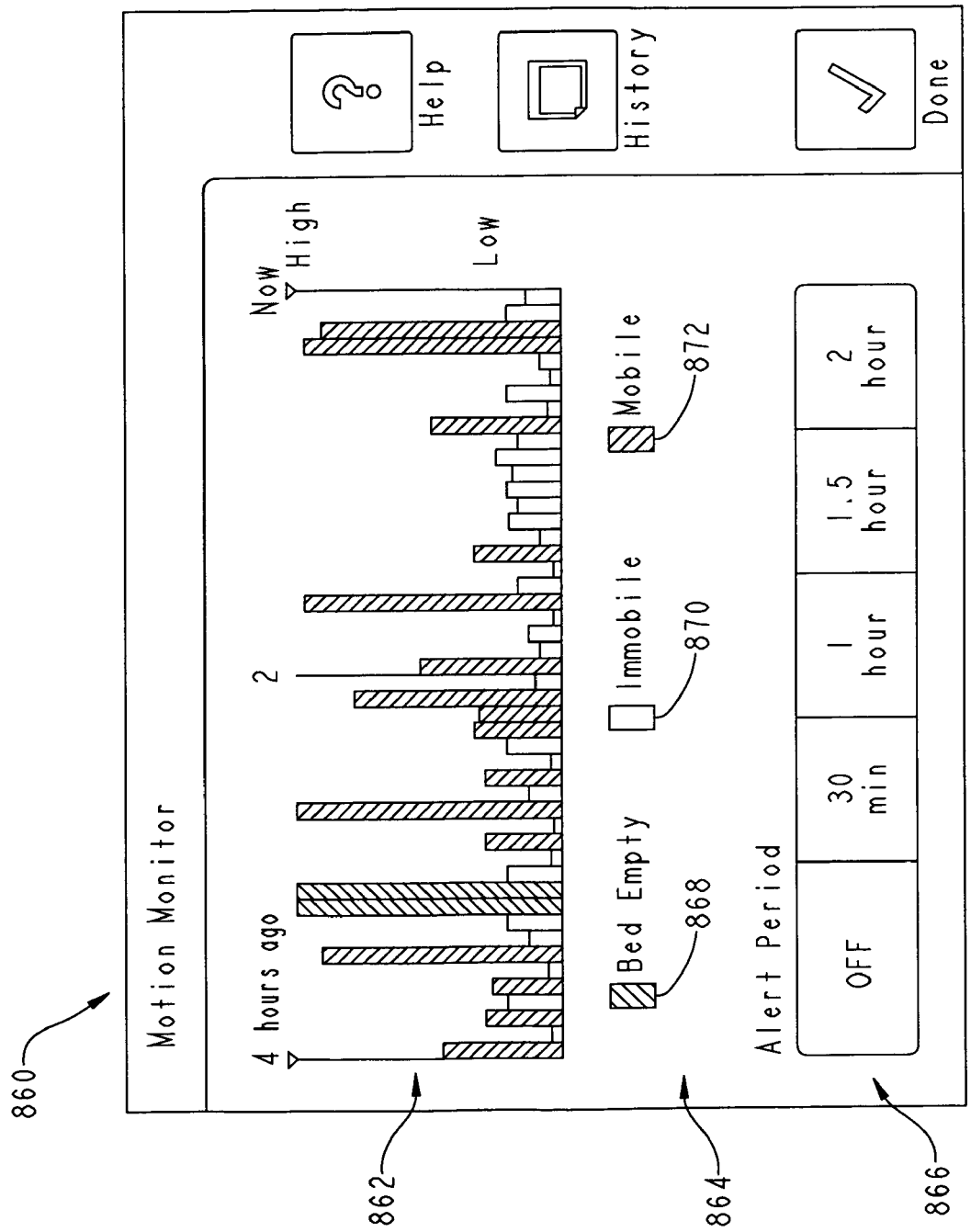
FIG. 14 is another embodiment of the screen display of the motion monitor user interface screen when the motion monitor is in the off condition.

FIG. 14 illustrates another embodiment of a screen display 860 of the present invention. In this embodiment, a first display portion 862 includes a bar graph. A second display portion 864 defines a state of the patient or bed corresponding to each of the bars of the first display portion 862. These states include bed empty, immobile, and mobile. A third display portion 866 enables a caregiver to select the alert period over which patient movement is monitored to provide an alarm. For the embodiment of FIG. 14, the width of each of the bars displayed in part in 862 is 5 minutes. In this embodiment, the interface does not provide for the selection a threshold level. Instead the threshold level is set internally in the firmware residing in the algorithm control unit 526.

In FIG. 14, the alert period has been turned off. Consequently, while it is possible to see patient movement status which includes a bed empty status 868, a patient immobile status 870, and a mobile status 872, the system is not placed into an alarm mode where an alarm is provided as previously described. In this mode, the system automatically graphs patient motion, immobility, as well as out of bed or bed empty status in a 4 hour rolling graph. The caregiver may access the graph by pressing the motion monitor button which is present in a menu. In the case of immobility, the Braden scale has been used where immobile is defined as breathing, wiggling extremities, and turning the head side to side.

Figure 15:
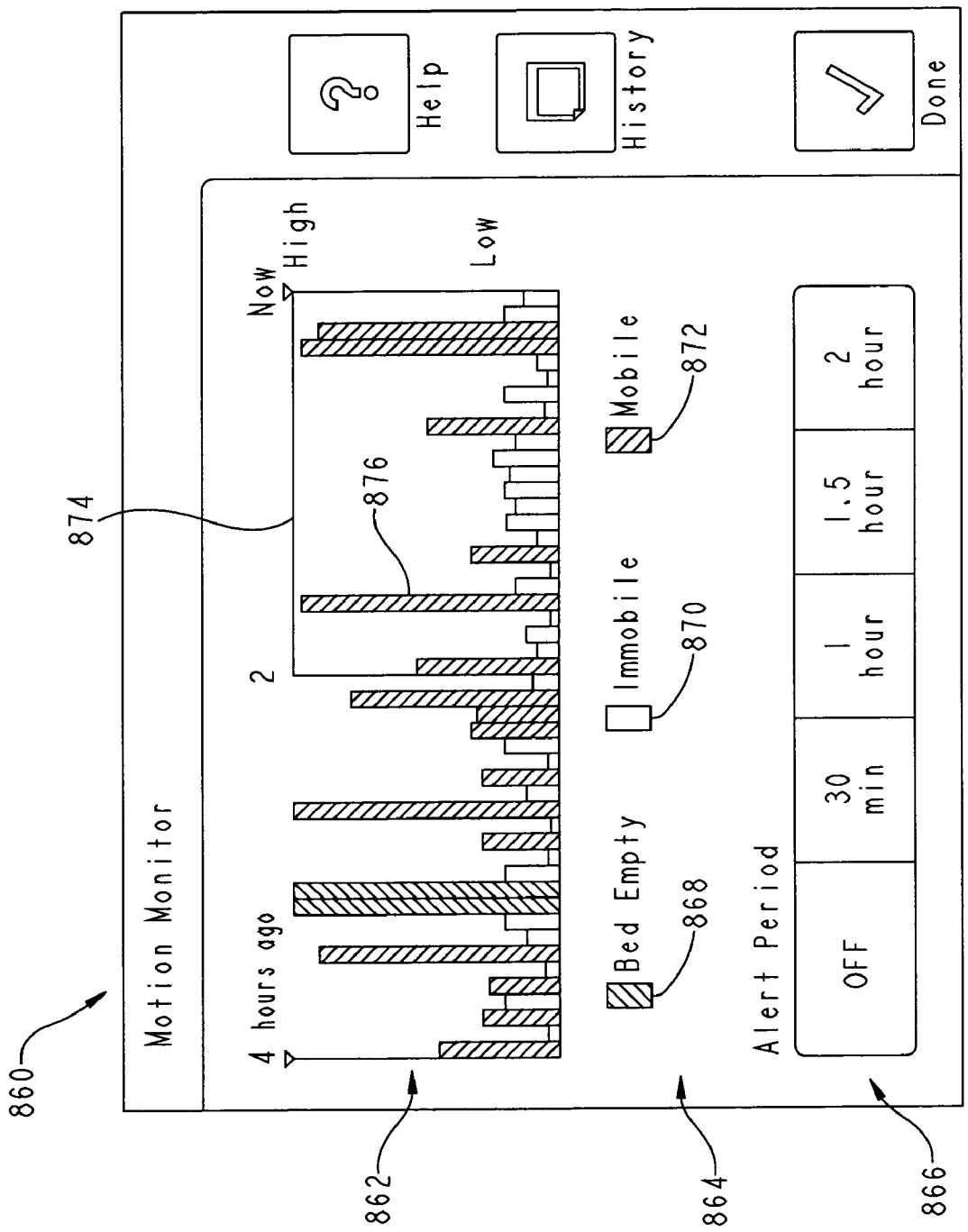
FIG. 15 is the screen display of FIG. 14 including the motion monitor alert set to 2 hours.

Referring now to FIG. 15, the caregiver has selected a 2 hour time period which establishes an alarm period for determining whether or not a patient is immobile during that time. The user interface 860 indicates that a 2 hour time period has been selected by displaying a rectangle 874 from the current time to a time of 2 hours previous. The two hour time period includes a plurality of mobile states 876, thereby indicating that the patient has sufficient mobility. In this instance, an alarm is not sounded.

Figure 16:
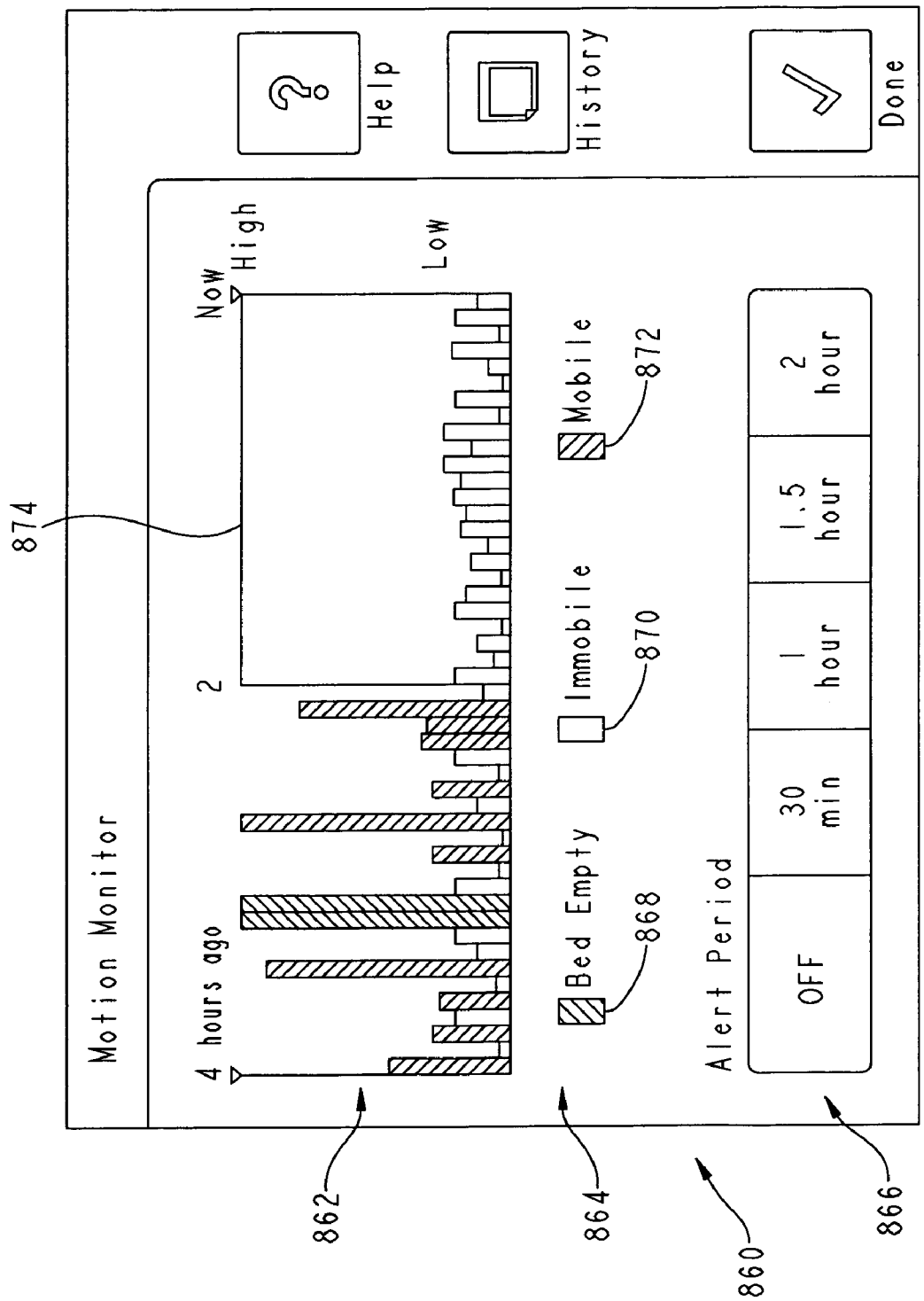
FIG. 16 is the screen display of FIG. 14, including the motion monitor alert set to set to 2 hours with motion considered to be immobile during the time period.

Referring now to FIG. 16, a screen display 860 is shown where a patient has been determined to be immobile for a selected 2 hour period. Only the immobile bars 870 are displayed over the 2 hour period 874. Consequently, the patient has remained immobile for the entire time. Since none of the mobile states 872 have occurred during the 2 hour window, an alarm would sound.

Figure 17:
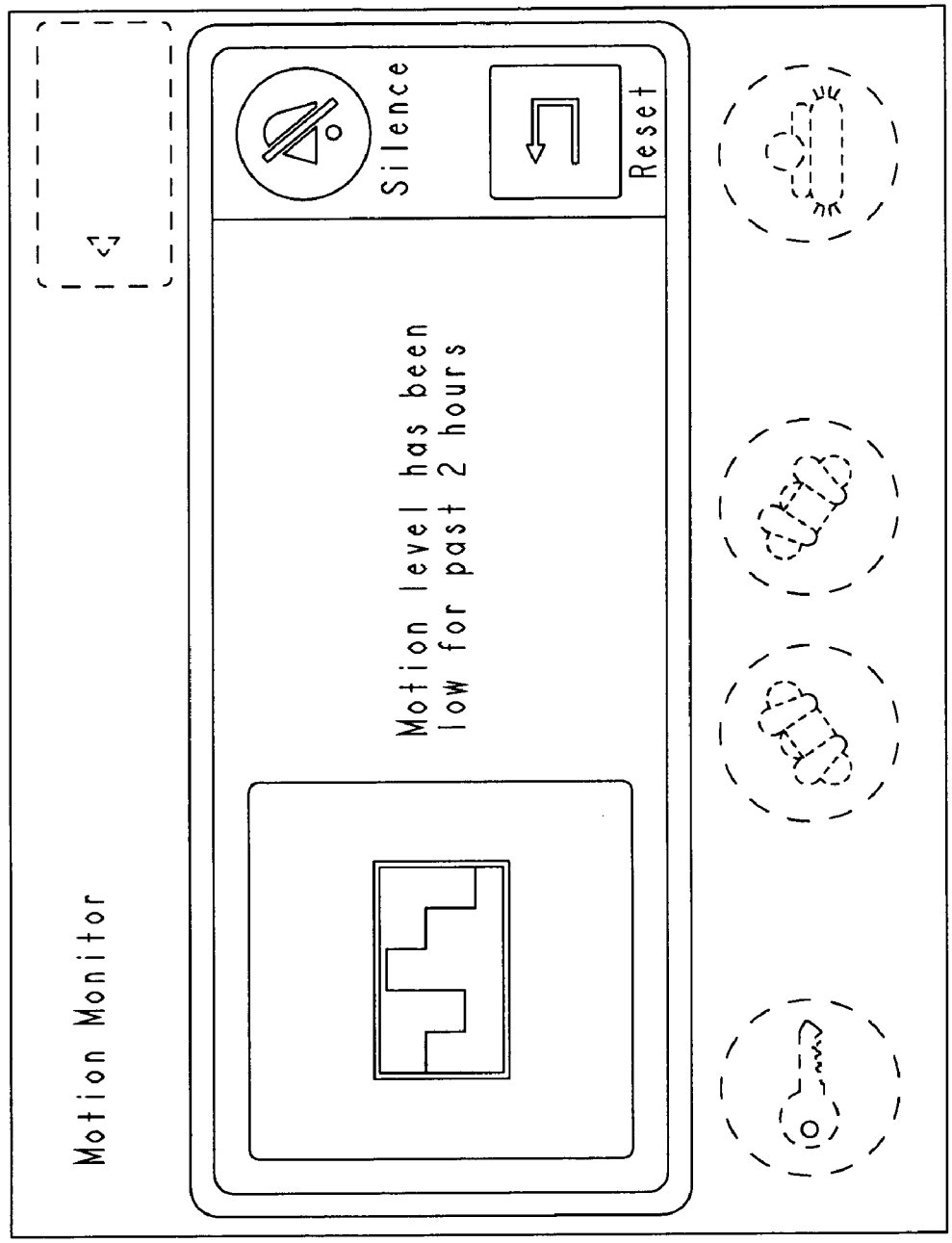
FIG. 17 is a screen display of the motion monitor user interface screen showing an alert notification if the motion level does not rise above the minimum motion level set in the motion monitor.

An audible alarm may be made with the speaker 530 of FIG. 4B. In addition, as illustrated in FIG. 17 a visual alarm is made on the user interface. A warning is displayed which states that the motion level has been low for the past 2 hours. A similar type of display may be used for those instances where a threshold level has been set such as described with respect to FIG. 12. In the embodiment, the warning may state that the motion level is under the threshold setting during the past 90 minutes if a 90 minute period has been selected.

While this invention has been described with specific embodiments thereof, alternatives, modifications and variations may be apparent to those skilled in the art. Accordingly, it is intended to embrace all such alternatives, modifications and variations that fall within the spirit and broad scope of this appended claims.

The invention claimed is:

1. In a pressure adjustable support, including a bladder assembly having a plurality of bladders to support a patient, a plurality of sensors, each of the plurality of sensors subtending at least one of the bladders to sense a force transmitted through the bladders, a method comprising the steps of:
 setting a time period for determining an activity level;
 setting a threshold level with respect to the sensed force;
 sampling the forces sensed by each of the plurality of sensors transmitted through the bladders;
 filtering the sampled forces to determine a high frequency component;
 determining which of the filtered sampled forces exceed the set threshold level;
 determining the number of filtered sampled forces determined to cross the threshold level; and
 generating a signal as a function of the set time period, the set threshold level, and the sampled forces.

2. The method of claim 1, the step of sampling the forces sensed by each of the plurality of sensors including sampling over a predetermined period of time the forces sensed by each of the plurality of sensors.

3. The method of claim 1, comprising the step of determining the amount of time the filtered sampled forces exceed the threshold level during the predetermined period of time.

4. The method of claim 3, comprising the step of determining a sum of the total amount of the filtered sampled forces exceeding the threshold level.

5. The method of claim 4, further comprising the step of determining the maximum filtered sampled force.

6. The method of claim 5, further comprising the step of storing the maximum filtered sampled force.

7. The method of claim 5, further comprising the step of determining a weight for at least one of the number of filtered sampled forces exceeding the threshold level, the amount of time the filtered sampled forces exceed the threshold level during the predetermined period of time, sum of the total amount of the filtered sampled forces exceeding the threshold level, and the maximum filtered sample force.

8. The method of claim 1, wherein the bladder assembly includes a plurality of vertically oriented bladders.

9. The method of claim 8, wherein the bladder assembly includes an air chamber shared by each of the plurality of vertically oriented bladders.

10. The method of claim 1, wherein each of the plurality of sensors comprise a light responsive device disposed in a compressible medium.

11. The method of claim 10, the step of sampling the forces sensed by each of the plurality of sensors including sampling the forces in a predetermined order.

12. The method of claim 11, the step of sampling the forces in a predetermined order wherein the predetermined order includes sampling the forces consecutively from non-adjacent sensors.

13. A motion monitor device for monitoring the motion of a patient lying on a hospital bed, including a mattress comprising;
a plurality of bladders;
a plurality of sensors subtending at least one of the bladders;
a motion monitor operably coupled to the sensors and configured to sample forces sensed by each of the sensors over a time period, set a threshold level with respect to the sensed forces, filter the sampled forces to determine a high frequency component, determine which of the filtered sampled forces exceed the threshold level, and determine a number of the filtered sampled forces that exceed the threshold force level; and
a user interface device, operatively coupled to the motion monitor, the user interface device including a screen to display motion information and an input device to input motion parameters to determine patient motion.

14. The motion monitor device of claim 13, wherein the input devices includes a time period selector to select a time period over which the motion of the patient is determined.

15. The motion monitor device of claim 14, wherein the input device includes a threshold selector to select a threshold for movement above which the patient is determined to be mobile.

16. The motion monitor device of claim 15, wherein the input device includes a history selector to select a history of the monitored motion.

17. The motion monitor device of claim 15, wherein the user interface device includes an alarm to indicate when motion of a patient over time falls below the selected threshold level.

18. The motion monitor device of claim 13, further including a processor operatively coupled to the user interface device and to the plurality of sensors, the processor to received the motion parameters from the input device and to transmit information to the screen.

19. The motion monitor device of claim 18, wherein the processor generates a mobile signal responsive to movement of a patient sensed by the plurality of sensors for display on the screen.

20. The motion monitor device of claim 19, wherein the processor generates an immobile signal responsive to movement of a patient sensed by the plurality of sensors for display on the screen.

21. The motion monitor device of claim 20, wherein the processor generates a bed empty signal responsive to an empty bed sensed by the plurality of sensors for display on the screen.

* * * * *